United States Patent
Zanata et al.

(10) Patent No.: US 11,273,322 B2
(45) Date of Patent: Mar. 15, 2022

(54) APPARATUS FOR SCANNING LASER THERAPY

(71) Applicant: K-LASER D.O.O., Sezana (SI)

(72) Inventors: Francesco Zanata, Treviso (IT); Mauro Zanata, Treviso (IT); Andrea Zanata, Treviso (IT); Enrico Zanata, Treviso (IT)

(73) Assignee: K-LASER D.O.O., Sezana (SI)

( * ) Notice: Subject to any disclaimer, the term of this patent is extended or adjusted under 35 U.S.C. 154(b) by 128 days.

(21) Appl. No.: 16/620,346

(22) PCT Filed: Jun. 7, 2018

(86) PCT No.: PCT/IB2018/054097
§ 371 (c)(1),
(2) Date: Dec. 6, 2019

(87) PCT Pub. No.: WO2018/225000
PCT Pub. Date: Dec. 13, 2018

(65) Prior Publication Data
US 2020/0179714 A1    Jun. 11, 2020

(30) Foreign Application Priority Data

Jun. 8, 2017 (IT) .......................... 102017000062592

(51) Int. Cl.
*A61N 5/06* (2006.01)
*A61N 5/01* (2006.01)
*A61N 5/067* (2006.01)

(52) U.S. Cl.
CPC ............. *A61N 5/0616* (2013.01); *A61N 5/01* (2013.01); *A61N 5/067* (2021.08);
(Continued)

(58) Field of Classification Search
CPC .. A61N 5/0616; A61N 2005/067; A61N 5/01; A61N 2005/0633; A61N 2005/0626;
(Continued)

(56) References Cited

U.S. PATENT DOCUMENTS

2001/0023363 A1* 9/2001 Harth ................. A61K 41/0057
607/90
2001/0053907 A1* 12/2001 Ota ...................... A61B 18/203
606/10

(Continued)

FOREIGN PATENT DOCUMENTS

EP          1163887 A1    12/2001
WO     2004098710 A1    11/2004
(Continued)

OTHER PUBLICATIONS

International Search Report, issued in PCT/IB2018/054097, dated Oct. 8, 2018, Rijswijk, Netherlands.

*Primary Examiner* — Carl H Layno
*Assistant Examiner* — Aya Ziad Bakkar
(74) *Attorney, Agent, or Firm* — Moore & Van Allen PLLC; Henry B. Ward, III

(57) ABSTRACT

An apparatus for laser therapy comprises a frame on which a plurality of lasers slide at several wavelengths in motorized and automated manner for applying the laser on and through the skin and mucous membranes of a patient. The frame is also motorized, allowing installation on the patient without moving the patient from bed. The apparatus is programmed to determine treatment autonomously on the basis of parameters determined by the apparatus during pretreatment and to vary treatment parameters in real time for treatment optimization and safety purposes.

29 Claims, 13 Drawing Sheets

(52) U.S. Cl.
CPC ............... *A61N 2005/0628* (2013.01); *A61N 2005/0642* (2013.01); *A61N 2005/0659* (2013.01)

(58) Field of Classification Search
CPC .......... A61N 2005/0642; A61B 18/203; A61B 18/20
See application file for complete search history.

(56) References Cited

U.S. PATENT DOCUMENTS

| | | | | |
|---|---|---|---|---|
| 2010/0324426 | A1* | 12/2010 | Tucek | A61B 5/1077 600/476 |
| 2012/0116373 | A1* | 5/2012 | Moench | A61B 18/203 606/9 |

FOREIGN PATENT DOCUMENTS

| | | | | |
|---|---|---|---|---|
| WO | WO-2004098710 | A1 * | 11/2004 | ............... A61N 5/04 |
| WO | 2016203461 | A1 | 12/2016 | |
| WO | WO-2016203461 | A * | 12/2016 | ........... A61B 5/0077 |

\* cited by examiner

APPARATUS FOR SCANNING LASER THERAPY

CROSS-REFERENCE TO RELATED APPLICATIONS

This application is filed under the provisions of 35 U.S.C. 371 as national stage of International Patent Application No. PCT/IB2018/054097, filed on Jun. 7, 2018 entitled "APPARATUS FOR SCANNING LASER THERAPY" in the name of Francesco Zanata et al., which claims priority to Italian Patent Application No. 102017000062592 filed on Jun. 8, 2017, both of which are hereby incorporated by reference herein in their entirety.

FIELD OF THE INVENTION

The present invention relates to an apparatus for scanning laser therapy.

More precisely, the present invention relates to a medical apparatus which has a frame on which a plurality of multiple wavelengths lasers are made to slide in motorized and automated manner for applying the scanning laser onto and through the skin and mucous membranes of a patient. The frame itself is also motorized, whereby allowing its installation on the patient without the person needing to move from their bed. The apparatus is programmed so as to determine the choice of treatment autonomously on the basis of parameters determined by the device itself during the pretreatment step and vary the treatment parameters in real time for treatment optimization and safety purposes.

BACKGROUND OF THE INVENTION

Traditional laser devices for therapeutic purposes envisage static parameter setting modes, every setting is based on a standard therapeutic indication and no specific adjustment based on real tissue absorption and on the desired effects according to the individual patient's therapeutic needs are provided.

Actually, in such devices the patient's absorption profile is not even automatically assessed.

The emission power setting is such to be fixed for all wavelengths used in a treatment, or divided between all wavelengths, without a specific balancing mode according to the effects to be achieved on the patient, but only in order not to exceed the safety temperature for the tissue.

The power in some conventional devices may vary during the treatment, but only according to the principle of not exceeding the maximum allowed skin temperature. For this purpose, in some traditional lasers, temperature is controlled by a thermal sensor, solely for the purpose of not burning the patient.

The modulation frequency setting is such to be fixed for all wavelengths used. In the cases in which modulation frequency is varied during the treatment, the variation is identical for all wavelengths without such variation being calibrated to achieve specific therapeutic effects.

On some traditional lasers, the user is prompted to choose the patient's skin photo-type, this setting remaining the sole opinion of the physician on the basis of visual diagnosis and not determined by an automatic system.

An apparatus for administering a laser therapy, in which a patient is irradiated from above and from below a bed, is known from patent application US2010324426A. To do this, the bed is equipped with movable slats, so that one linear zone of the body can be treated at a time. This device is complicated and the method for modifying it (moving the slats) during the treatment is extremely heavy and long, requiring the continuous presence of an operator (therapist). The same patent application relates to a laser therapy machine in which the patient is seated and an entire laser (generator (diode) and irradiation head) is made to move along a horizontal arched support which is also made to translate vertically. This arrangement is equally complicated and very difficult to implement, because the positioning of the patient is difficult and the motor equipment for moving the laser generator becomes increasingly larger as the laser power increases. Such structure may not be suited for medium- or high-intensity therapy and shows mechanical problems also for low-intensity therapies. The described apparatus also uses a feedback given by a proximity sensor integral with the movable laser device to maintain a uniform distance from the patient's body. There are no on-the-fly adjustments of the laser in order to maximize the effect of the therapy and minimize the risks for the patient.

An apparatus for administering a laser therapy, similar to the one described above, is also known from patent application EP1163887A1. Again here, there are no on-the-fly adjustments of the laser in order to maximize the effect of the therapy and minimize the risks for the patient. Furthermore, in this system, the laser head is raised and lowered and this is very dangerous, for example if the patient raises an arm. The problem of uncontrolled heating of the patient's skin is solved in a very unsatisfactory manner by sending a jet of cold air onto the skin. Still, the laser head is moved remotely by means of a joystick. The whole system is therefore operator-dependent.

Additionally, the systems according to the prior art are based on static therapeutic parameters, which manage a treatment by setting the power, the modulation, the treatment time and, in some devices, also the wavelength, whereby transferring a given energy to the patient. These data for therapeutic protocols are obtained from standard studies and are almost never corrected or optimized for the specific treatment, whereby resulting in a loss of effectiveness. Incidentally, the machines on the market have no means to be more adaptable.

It is an object of the present invention to provide a device which solves the problems and overcomes the drawbacks of the prior art.

It is the object of the present invention a device according to the appended claims, which form an integral part of the present description.

DETAILED DESCRIPTION OF EXAMPLES OF PREFERRED EMBODIMENTS OF THE INVENTION

Throughout this description and in the appended claims, it is understood that the word "comprises" can be replaced by the expression "consists of". Furthermore, elements of the embodiments may be extracted from them and used also independently from the other elements and details.

The illustrated and suggested embodiments may be combined.

Foreword on Absorption Definition and Calculation

Figure 1:
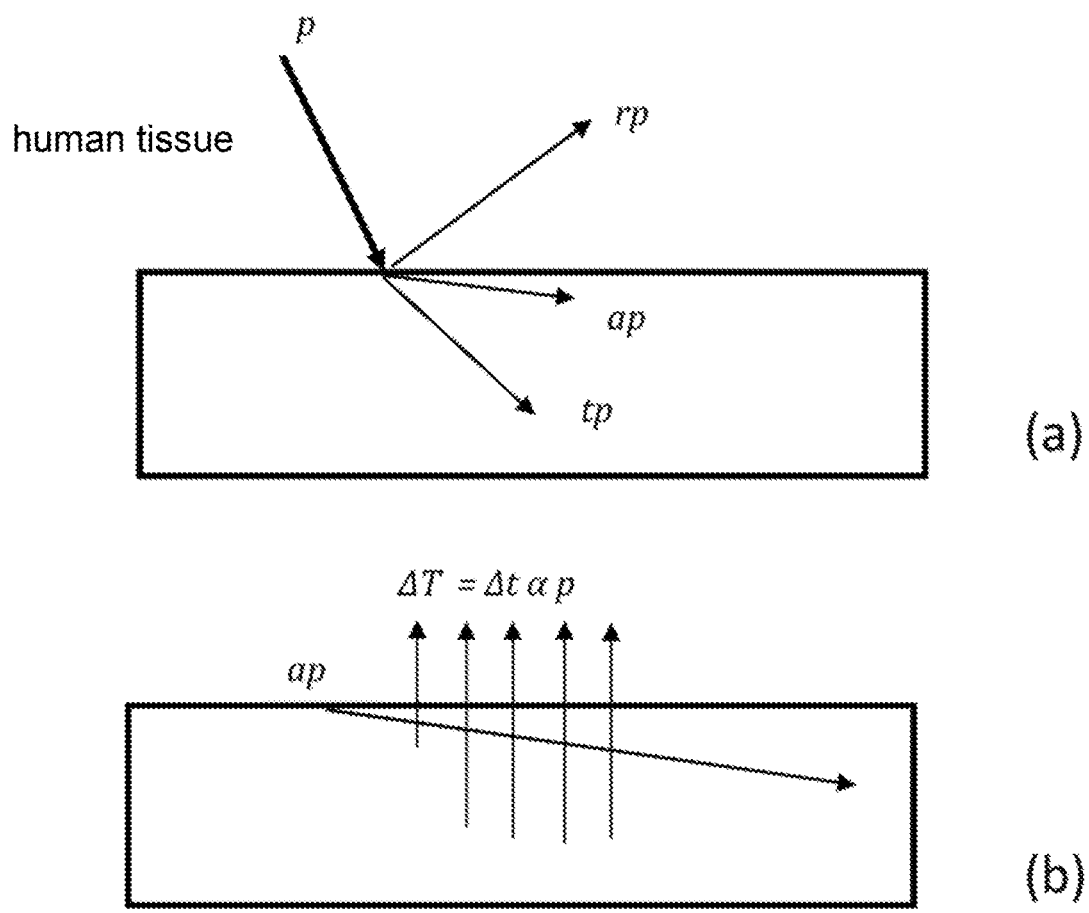
FIG. 1 shows a chart of the reaction of the skin to laser irradiation, according to common scientific knowledge.

With reference to FIG. 1, the incident irradiation of the laser power p on a non-punctiform surface in the skin/body is broken down into reflected irradiation rp, absorbed irradiation ap, as absorbed by the surface layers, and transmitted radiation tp, as transmitted in the deeper layers of the body.

The absorbed and transmitted radiation depends on the physical properties of the tissue, such as color and composition (e.g. amount of water of the tissue, blood, melanin, and all the tissue chromophores).

Figure 2:
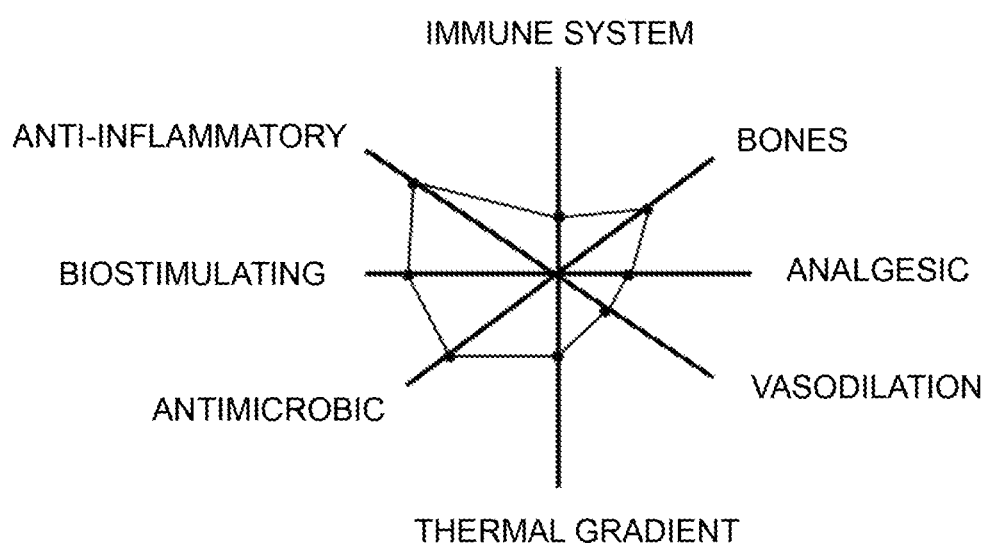
FIG. 2 shows an example of a Kiviat diagram used to set the effects of the therapy one desires to achieve by using the device of the present invention.

With reference to FIG. 2, according to the invention, the method firstly sets on the device which and how many effects are to be obtained from the laser treatment.

Figure 3:
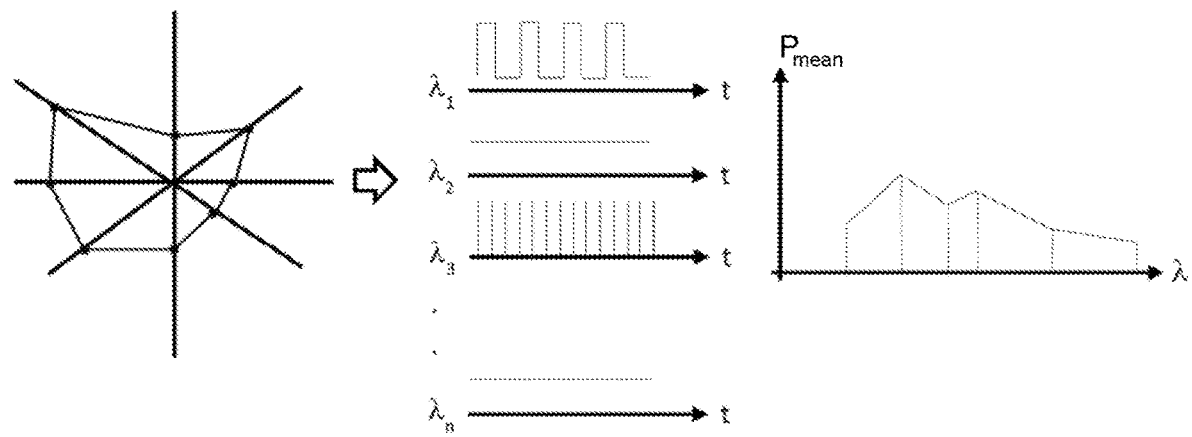
FIG. 3 shows a diagram which illustrates the steps (from the left) of choosing the therapy, obtaining the various laser emission wavelengths and of distributing the average powers of the various wavelengths, according to the present invention.

With reference to FIG. 3, the physician's choice is processed by means of an algorithm, which transforms the working modes of each laser of the device according to the invention having frequencies $\lambda_1, \lambda_2, \lambda_3, \lambda_4 \ldots \lambda_n$, respectively.

With reference to FIGS. 1(b), 4, 5(b), 5(c), 6, 7, a "pretreatment" test is performed on the patient, during which the absorptions are measured on the basis of body temperature, by measuring a variation $\Delta T_1$, $\Delta T_2$, $\Delta T_3$, $\Delta T_4$, ... $\Delta T_n$ for the respective wavelengths $\lambda_1, \lambda_2, \lambda_3, \lambda_4 \ldots \lambda_n$, whereby obtaining the absorption profile of the skin $\alpha_{\lambda 1}, \alpha_{\lambda 2}, \alpha_{\lambda 3}, \alpha_{\lambda 4}, \ldots \alpha_{\lambda n}$.

With reference to FIG. 1(b), with regards to the surface portion, α will indicate the general absorption of the skin. The absorbed radiation in the first skin layers is transformed into the temperature increase ΔT in a time Δt which can be measured by the sensor integrated in the laser emission head of the device according to the invention.

Specifically, we have similar definitions for each wavelength. Having predetermined a constant surface power and a short time Δt, the temperature difference ΔT is measured between the start and end of the laser emission at length $\lambda_i$ ($\Delta T_{\lambda_i}$), so as to determine an absorption $\alpha_{\lambda,i}$.

Alternatively and preferably, having predetermined a maximum temperature $T_{max}$ to be reached on the skin surface, such as not to cause pain/burns, the time required Δt to reach such temperature is measured starting from a minimum predetermined temperature, so as to obtain $\alpha_{\lambda,i}$.

The coefficient $\alpha_{\lambda,i}$ indicates the temperature increase of the skin when a laser light of average power p is applied on a non-point-like surface and non-null area (e.g. a unitary surface). $\alpha_{\lambda,i}$ is the inverse of the thermal capacity of the skin, and, since it is strongly dependent on the absorbed wavelength $\lambda_i$ it will be named "skin absorption" for the sake of simplicity. In both method alternatives above we have:

$$\alpha_{\lambda_i} = \frac{\Delta T_{\lambda_i}}{\Delta t} \frac{1}{p} i = 1 \ldots n \tag{1}$$

$$\alpha_\lambda = \{\alpha_{\lambda_1}, \alpha_{\lambda_2}, \ldots, \alpha_{\lambda_n}\} \tag{2}$$

$\alpha_{\lambda,i}$ is measured in Kelvins/Joules.

The device obtains the body-skin profile on the basis of the ΔT° C. detected for the different λ.

In more detail, with reference to the preceding figures, absorption αλ is measured by measuring the patient's skin temperature. If the instantaneous measured temperature $T^t$ is lower than a temperature $T_{min}$, the method continues; otherwise, the laser application position on the skin is changed and the methods starts again.

The device continuously emits predetermined low power (e.g. 1 W) (starting from wavelength 1 up to n, in any order), and the irradiation continues to temperature $T^t < T_{min}$.

At this point, a computerized calculation unit calculates the time to reach a second temperature $T_f = T_{max}$. On the basis of the previous formula, $\alpha_\lambda$ is calculated (see formula (1) above).

The cycle starts again proceeding with the calculation of the absorptions, emitting the successive wavelengths λ.

Considering a superposition of the effects, the laser head identifies a single temperature difference during the treatment, to be considered as the sum of the temperature contributions of the different wavelengths:

$$\Delta T = \Delta T_{\lambda_1} + \Delta T_{\lambda_2} + \ldots + \Delta T_{\lambda_n} \tag{3}$$

$$\Delta T = \Delta t (\alpha_{\lambda_1} p_{\lambda_1} + \alpha_{\lambda_2} p_{\lambda_2} + \ldots + \alpha_{\lambda_n} p_{\lambda_n}) \tag{4}$$

Figure 4:
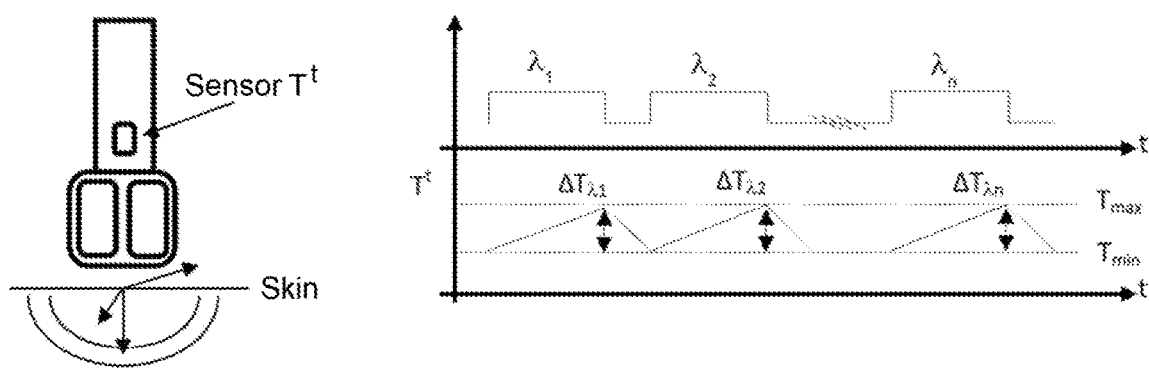
FIG. 4 shows the step of measuring absorptions according to the body temperature measured during a "pretreatment" during which the various wavelengths are emitted in sequential manner.

The $\alpha_{\lambda,n}$ determine a profile for adjusting the powers (average or peak) during treatment, so as not to exceed a predetermined temperature (FIG. 4).

Figure 8:
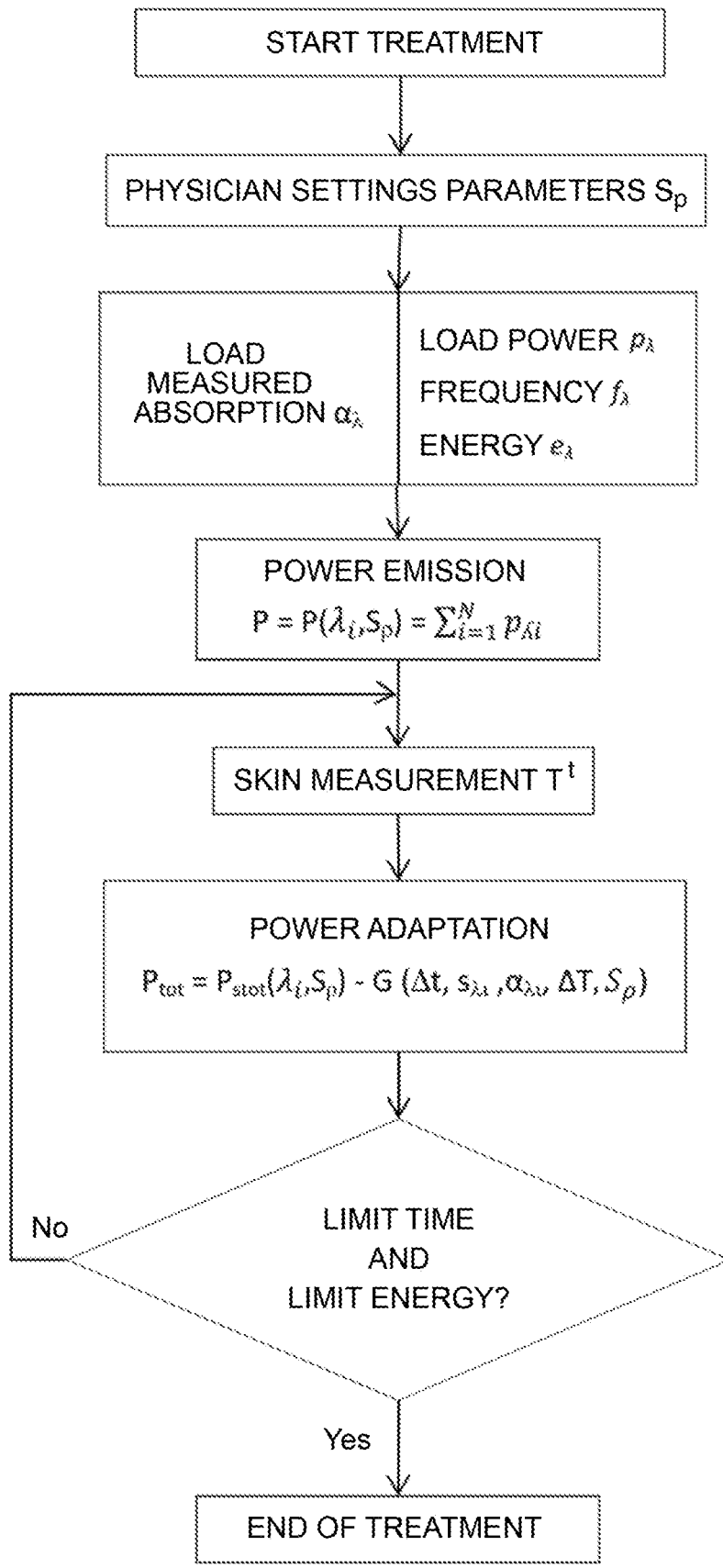
FIG. 8 shows the detailed flow chart of the parameter calculation and treatment step of the method according to the invention.

After having measured these absorptions, with reference to FIG. 8, the method proceeds with the successive processing and laser treatment steps.

At the start of the treatment, the physician chooses a set of parameters displayed on screen, e.g. represented in the form of a Kiviat diagram. The set of these parameters will be called S and will be described in details below. The power emitted during the treatment will be correlated to the temperature measured by the temperature sensor, therefore, on the basis of the detected temperature, the device will change the power (peak or average), frequency and duty cycle parameters in real-time so as to follow the powers and frequencies deriving from the processing of the profile parameters S chosen at the onset by the physician and limiting the skin surface temperature to a safe maximum temperature.

Figure 5:
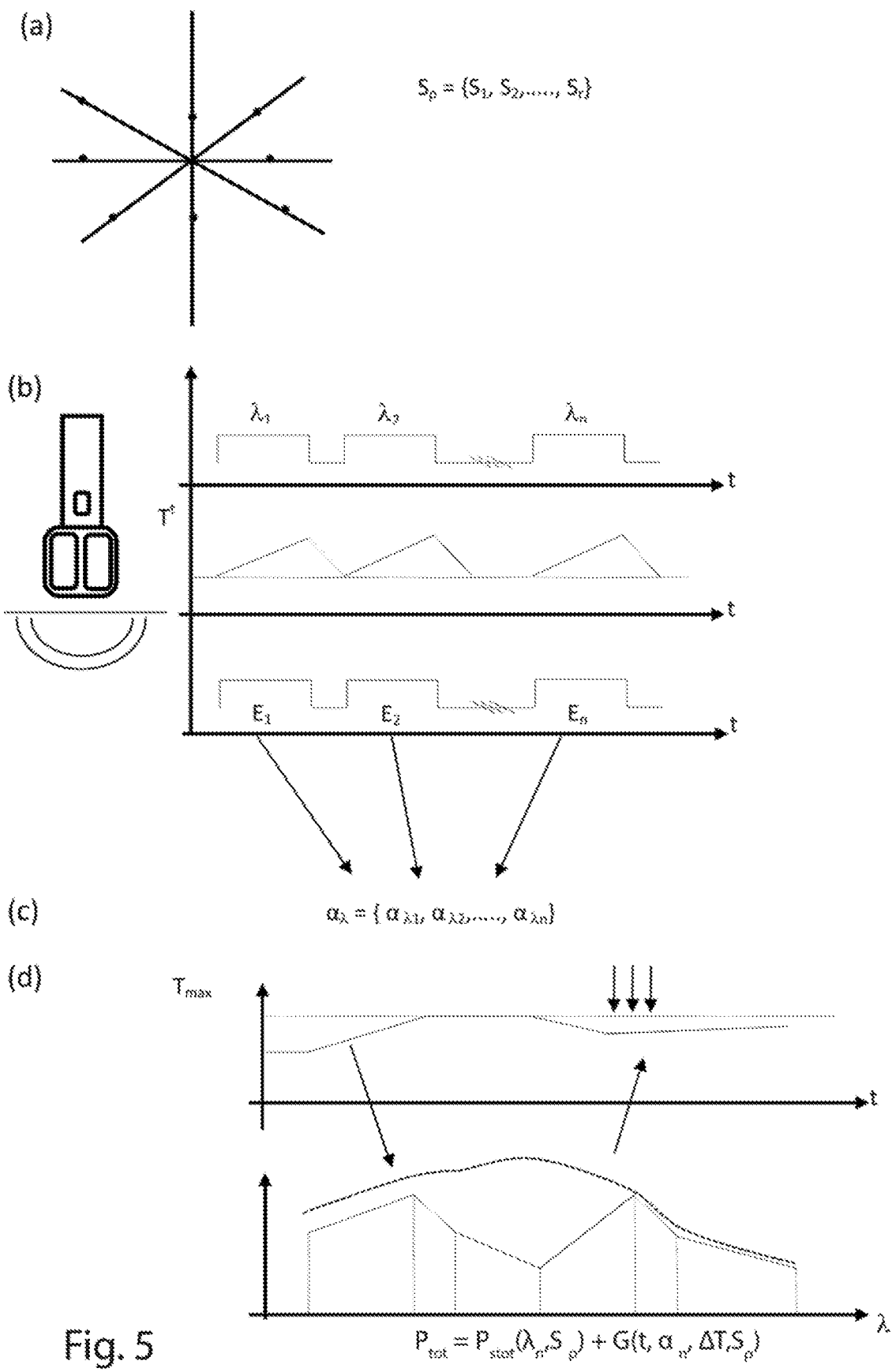
FIGS. 5a-5d show the various steps of the method according to the invention, from the Kiviat diagram (a) to pretreatment step (b), for each individual patient or based on common characteristics of a set of potential patients, whereby obtaining absorptions (c); treatment on the basis of the determined parameters (d) with real-time feedback.
Figure 6:
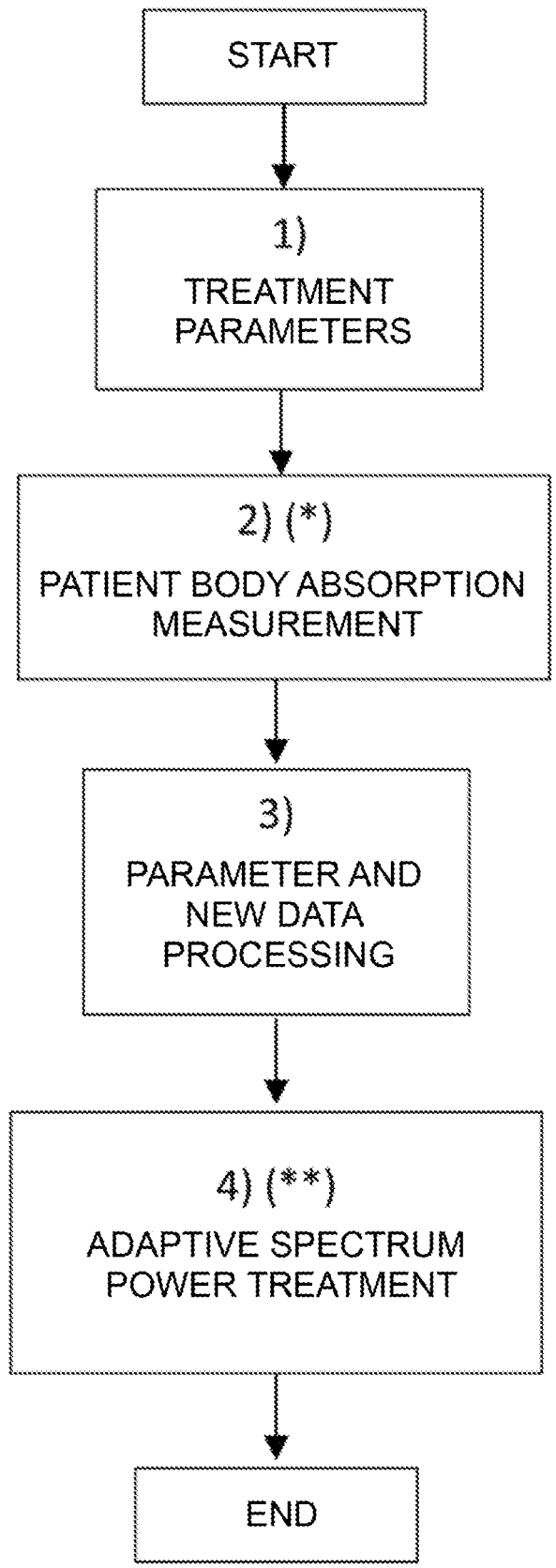
FIG. 6 shows a flow chart which describes the method in FIG. 5.
Figure 7:
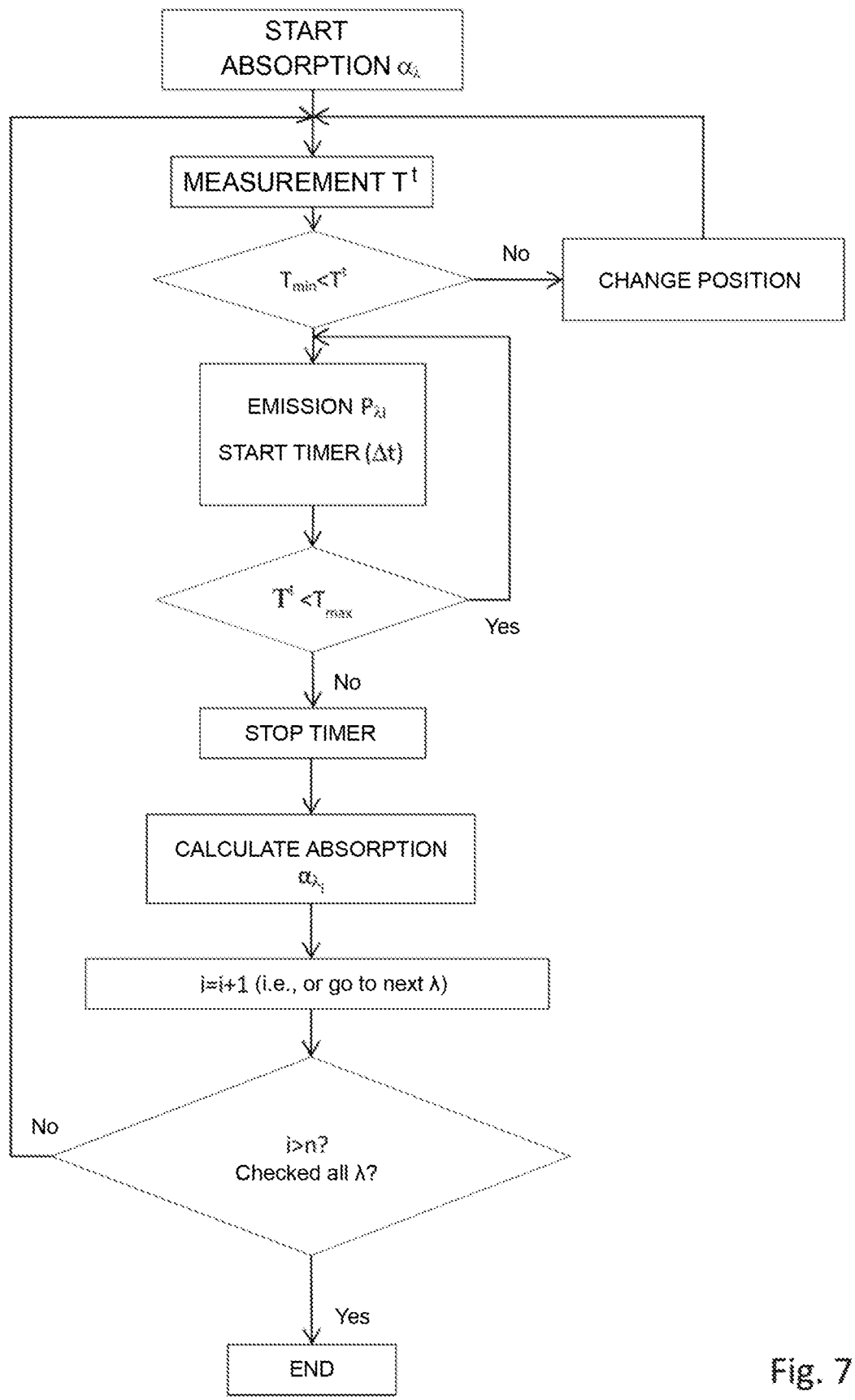
FIG. 7 shows the detailed flow chart of the pretreatment step.

FIG. 5d shows a chart of the adaptive spectral power treatment according to the present invention, in which the power depends on the parameters described hereto:

$$P_{tot} = P_{stot}(\lambda_1, \lambda_2, \ldots \lambda_n, S_\rho) - G(t, \alpha_{\lambda,1}, \alpha_{\lambda,2} \ldots, \alpha_{\lambda,n}, \Delta T, S_\rho) \quad (5)$$

wherein t is the instantaneous time and $S_\rho = \{s_1, s_2 \ldots s_r\}$ is the set of r (with r being a positive integer, and $\rho = 1, 2, \ldots, r$), i.e. initial parameters chosen by the user. In particular, for the only sake of simplification for medical staff, such parameters can be made to correspond to points of a Kiviat diagram, as shown in FIG. 2.

The function $P_{stot}$ is a method which transforms the parameters chosen by the physician into a power which will be emitted by the device during the treatment. Such method can be based, for example, on the use of look-up tables and interpolation algorithms. Analytical expressions can also be used for the function $P_{stot}$, or other optimization algorithms (e.g. statistical), according to cases and conveniences.

G is a feedback function (FIG. 10) which modifies the parameters processed by $P_{stot}$ according to the temperature read by the sensor.

The physician sets the treatment parameters (see FIG. 2). The calculation unit loads the measured absorptions $\alpha_\lambda$ as from a physical memory.

The physician performs the treatment with powers $p_{\lambda,i}$ for $i = 1, \ldots, n$ for the various wavelengths, in which the total power is $P_{stot} = \Sigma_{i=1}^n p_{\lambda,i}$ (lowercase p means single power, uppercase P means the sum).

The skin temperature $T^t$ in the treatment area is measured during the treatment and the power parameters are adapted on the basis of this temperature according to the aforesaid function G. When a preset time limit or a preset maximum irradiated energy (or "limit") is reached, the treatment is concluded (maximum energies or maximum times of the entire treatment are predetermined by persons skilled in the art, e.g. empirically, according to the desired therapy and the body area to be treated).

Describing the method in more detail, be n the number of wavelengths $\lambda$ that the device according to the invention can emit.

P is a set of powers p emitted by the various wavelengths of the device:

$$P_\lambda = \{p_{\lambda,1}, p_{\lambda,2}, \ldots, p_{\lambda,n}\}$$

Be $\gamma$ a step, i.e. the emission of a plurality of laser beams having a wavelength $\lambda_1, \lambda_2, \ldots \lambda_n$, with respective powers $p_{\lambda,1}, p_{\lambda,2}, \ldots p_{\lambda,n}$, frequencies $f_{\lambda,1}, f_{\lambda,2}, \ldots, f_{\lambda,n}$, and duty-cycles $\delta_{\lambda,1}, \delta_{\lambda,2}, \ldots, \delta_{\lambda,n}$, which are emitted with the respective energies $e_{\lambda,1}, e_{\lambda,2}, \ldots, e_{\lambda,n}$:

$$\gamma = \{\lambda_i, p_{\lambda,i}, f_{\lambda,i}, \delta_{\lambda,i}, e_{\lambda,i}\} \text{ with } i = 1 \ldots n$$

$$\gamma = \begin{bmatrix} \lambda_1 & \cdots & e_{\lambda n} \\ \vdots & \ddots & \vdots \\ \lambda_n & \cdots & e_{\lambda n} \end{bmatrix}$$

It is worth noting here that $\gamma$ may also depend on $p_{\lambda,i}$ without $\delta_{\lambda,i}$ or vice versa because they both have the adjustment of the average power which is the one which contributes to the overheating of the patient as a consequence. In the first case, the duty-cycle may also be kept fixed in therapeutic treatments to a predetermined value.

Let $\Gamma$ be a treatment, i.e. a set m of steps $\gamma$:

$$\Gamma = \{\gamma_1, \gamma_2, \ldots, \gamma_m\}$$

Without complicating the notation, it is worth noting that for different steps $\gamma_1, \gamma_2, \ldots, \gamma_m$, the wavelengths will always be the n above, while the other values of the matrix may be different from step to step in general.

S is a number r of points of the Kiviat diagram (or other equivalent diagram or a different starting diagram but which makes it possible to choose the medical parameters or simply a number of initial parameters set in any manner). These points represent the number of therapeutic effects desired by the physician, wherein each element has a weight s between 0 and 1:

$$S = \{s_1, s_2, \ldots, s_r\} \quad 0 \leq s_j \leq 1$$

$$j = 1 \ldots r$$

The device contains a look-up table tab(P) in its memory which links the points S with a set of powers $P_{i,j}$. The set of the powers $P_{i,j}$ of each point and wavelength may be obtained from empirical results which maximize the effect representing j-th branch, or may be initial estimated values which are then adjusted over time.

The powers of each step of the treatment will be:

$$p_{\lambda,i} \in P_{i,j}$$

$$P_{i,j} = [p_{min\ i,j}, p_{max\ i,j}]$$

Given a point $s_j$ of a Kiviat axis which represents an effect correlated to the power, if we have $p_{min\ ij}$ in the zero position and we have $p_{max\ ij}$ in the maximum position, the therapy will be adapted to the point $p_{\lambda,i}$ chosen by the therapist between (with possible interpolation):

$$p_{\lambda,i}(s_j) = p_{min\ i,j} \text{ with } s_j = 0$$

$$p_{\lambda,i}(s_j) = p_{max\ i,j} \text{ with } s_j = 1$$

The exact value in this interval is calculated with a predetermined function, e.g. an interpolation function. This is because the physician in the experimentation step of the therapy determines the effective intervals and then the device decides what exact value to apply alone. This exact value will be called $p_{\lambda,i,j}(s_j) \in P_{i,j}$.

The power of each single wavelength which will be calculated as initial total therapy power with multiple wavelengths and multiple selected therapeutic effects, will be a combination of all the effects S:

$$p_{\lambda,i} = PS(p_{\lambda,i,j}(s_j); j = 1 \ldots r)$$

wherein PS is a preset function, e.g. a statistical function, in particular an arithmetic or weighed mean:

$$p_{\lambda,i} = \Sigma_{j=1}^r p_{\lambda,i,j}(s_j)$$

The total initial power of the treatment will be the sum of all the points of the matrix tab(P):

$$P_{stot}(\lambda_i, S) = \Sigma_{i=1}^n p_{\lambda,i}$$

tab(P) is shown below:

| tab(P) | $s_1$ | $s_2$ | $\ldots$ | $s_r$ |
|---|---|---|---|---|
| $\lambda_1$ | $P_{1,1}$ | $P_{1,2}$ | | $P_{1,r}$ |
| $\lambda_2$ | $P_{2,1}$ | $P_{2,2}$ | | $P_{2,r}$ |
| $\ldots$ | | | | |
| $\lambda_n$ | $P_{n,1}$ | $P_{n,2}$ | | $P_{n,r}$ |

The device contains a table tab(F) in its memory which links the points S of the Kiviat diagram to a set of frequencies $F_{i,j}$. The set $F_{i,j}$ is obtained from empirical results which maximize the effect representing the j-th axis, or may be initial estimated values, which are then optionally adjusted over time.

The frequencies (amplitude modulation) of each step of the treatment will be:

$$f_{\lambda,i} \in F_{i,j} F_{i,j} = [f_{min\ i,j}, f_{max\ i,j}] j=1 \ldots r$$

Given a Kiviat branch, which represents an effect correlated to frequency, if we have a measurement of the maximum interval $F_{i,j}$ in the position zero s and a measurement of the minimum interval $F_{i,j}$ in the maximum position s, the therapy will be adapted to point f chosen by the therapist, so that it is comprised between (with possible interpolation):

$F_{i,j}$max with $s_j=0$ $F_{i,j}$min with $s_j=1$

The exact value in this interval is calculated with a predetermined function, e.g. an interpolation function. This is because the physician in the experimentation step of the therapy determines the effective intervals and then the device decides what exact value to apply alone. This exact value will be called $f_{\lambda,i,j}(s_j) \in F_{i,j}$.

The modulation frequency of each individual wavelength will be calculated by any statistical function (e.g.: maximum search, minimum search, etc., on the intersection, union etc. of the intervals) which acts on the sets $F_{i,j}$:

$$f_{\lambda,i} = FS(f_{\lambda,i,j}(s_j)); j=1 \ldots r)$$

wherein FS is a preset function, e.g. a statistical function, in particular an arithmetic or weighed mean:

$$f_{\lambda,i} = \Sigma_{j=1}^{r} f_{\lambda,i,j}(s_j)$$

in the case of non-disjoint intervals. If instead the intervals are disjoint, then there will be as many successive steps as the disjoint intervals, while the function FS referred to above will be used for the others.

tab(F) is shown below:

| tab(F) | $s_1$ | $s_2$ | ... | $s_r$ |
|---|---|---|---|---|
| $\lambda_1$ | $F_{1,1}$ | $F_{1,2}$ | | $F_{1,r}$ |
| $\lambda_2$ | $F_{2,1}$ | $F_{2,2}$ | | $F_{2,r}$ |
| ... | | | | |
| $\lambda_n$ | $F_{n,1}$ | $F_{n,2}$ | | $F_{n,r}$ |

The device further contains a table tab(E) in its memory which links the points S of the Kiviat diagram with a set of energies $E_{i,j}$. The set $E_{i,j}$ is obtained from empirical results which maximize the effect representing the branch or may be initial estimated values.

The energies of each step of the treatment will be:

$e_{\lambda,i} \in E_{i,j}$ $E_{i,j} = [e_{min\ i,j}, e_{max\ i,j}]$

Given a Kiviat branch, which represents an effect correlated to the energy to be emitted in the treatment, if we have minimum energy $e_{min}$ in the zero position and maximum energy $e_{max}$ in the maximum position, each wavelength must emit an energy $e_{\lambda,i}$ such that:

$e_{\lambda,i}(s_j) = emin_{i,j}$ with $s_j=0$ $e_{\lambda,i}(s_j) = emax_{i,j}$ with $s_j=1$ The exact value in this interval is calculated with a predetermined function, e.g. an interpolation function. This is because the physician in the experimentation step of the therapy determines the effective intervals and then the device decides what exact value to apply alone. This exact value will be called $e_{\lambda,i,j}(s_j) \in E_{i,j}$.

The energy of each single wavelength which will be calculated as the initial total therapy energy with multiple wavelengths and multiple selected therapeutic effects will be a combination of all the effects S:

$$e_{\lambda,i} = ES(e_{\lambda,i,j}(s_j); j=1 \ldots r)$$

wherein ES is a preset function, e.g. a statistical function, in particular an arithmetic or weighed mean:

$$e_{\lambda,i} = \Sigma_{j=1}^{r} e_{\lambda,i,j}(s_j) e_{\lambda,i,j}(s_j) \in E_{i,j} j=1 \ldots r$$

tab(E) is shown below:

| tab(E) | $s_1$ | $s_2$ | ... | $s_r$ |
|---|---|---|---|---|
| $\lambda_1$ | $E_{1,1}$ | $E_{1,2}$ | | $E_{1,r}$ |
| $\lambda_2$ | $E_{2,1}$ | $E_{2,2}$ | | $E_{2,r}$ |
| ... | | | | |
| $\lambda_n$ | $E_{n,1}$ | $E_{n,2}$ | | $E_{n,r}$ |

The energies can be split into the steps in a homogeneous way or according to a distribution algorithm, which depends on the parameters S.

More details on the determination of the various steps of the method are provided below:

The method according to the invention may use different algorithms.

The first algorithm determines the number of steps of a treatment.

After the therapist has chosen the parameters S, the treatment $\Gamma$ is processed as a set m of successive steps $\gamma$:

$$\Gamma = \{\gamma_1, \gamma_2, \ldots, \gamma_m\}$$

For each wavelength, there may be multiple different modulation frequencies which make it possible to obtain the effects of the various parameters S. The number of steps M is thus the maximum number of necessary modulation frequencies between all wavelengths. So it is the maximum number of subsets $F_{\lambda,j}$ of the table tab(F) to which the frequency $f_\lambda$ belongs:

$$f_\lambda = \{f_{\lambda,1}, f_{\lambda,2}, \ldots, f_{\lambda,n}\}$$

being $f_\lambda$ the modulation frequency vector in a step. The number m of steps is obviously at most r (number of parameters).

The time t of each step will depend on the energy $E_{\lambda,j}$ obtained from tab(E).

It is worth specifying here that instead the powers and/or the duty-cycles will remain preferably the same for each step, so as to not influence the effects given by the modulation frequencies excessively. In all cases, the powers may also be varied provided that the empirical results justify the change. This is also possible because the powers in the table are given as intervals and so there is almost always a margin.

Since the power varies during the step (see function G which adjusts the total power), the total step time is variable and will be calculated on-the-fly by means of the function G (according to how much the skin is overheated).

Before treatment, we have an algorithm of:
a) DETERMINATION of the empirical powers $p_{\lambda,i}$ of each single step by means of the table tab(P), according to the Kiviat points S chosen by the physician (see above); the total power emitted by the device will be the sum of all $p_{\lambda_i}$ for i=1, ... n;

b) If the various frequency intervals determined for the various $\lambda_i$ have non-null intersection, DETERMINATION of the empirical frequencies $f_{\lambda_i}$ of each single step in the table tab(F), according to the Kiviat points S chosen by the physician (see above);

c) If the various frequency intervals determined for the various $\lambda_i$ have null intersection, optional DETERMINATION of the number of steps corresponding to the number of disjoint intervals among all intervals so as to administer the frequencies in succession;

d) Optional DETERMINATION of empirical energies $e_{\lambda_i}$ of each single step by means of table tab(E), according to Kiviat points S chosen by the physician; the total energy emitted by the device will be the sum of all $e_{\lambda_i}$ for i=1, ... n (the powers for each step may be the same or different according to possible empirical results or estimates).

During the treatment, we have an algorithm of:

e) FEEDBACK with temperature: i.e. the correction (reduction or increase) of average powers (in sequential or temporary manner) by varying the duty-cycles $\delta_{\lambda,i}$ (or by means of peak powers $p_{\lambda_i}$); such change is performed on the basis of the absorptions $\alpha_{\lambda,i}$ described above, e.g. proportionally thereto, so as to stabilize the temperature $T^t$ read by the sensor in the laser head.

Specific Examples of Application of the Method

The function G seen above is a correction of the treatment starting power $P_s(\lambda_i,S_\rho)$ and may be for example:

$$P_{tot}=P_s(\lambda_i,S_\rho)-G(t,\alpha_{\lambda,i},\Delta T,S_\rho)$$

Example of Power Calculation

We will see an example with two wavelengths $\lambda_1$, $\lambda_2$.

We will assume that there are 2 effects, so 2 Kiviat axes, called "BIOSTIMULATION", represented by $s_1$, "ANALGESIC", represented by $s_2$.

The user selects:
$s_1$=0.2
$s_2$=0.8

A table tab(P) is assumed:

| tab(P) | $s_1$ | $s_2$ |
|---|---|---|
| $\lambda_1$ | [0.5 W, 1 W] | [0.1 W, 2 W] |
| $\lambda_2$ | [0.1 W, 0.2 W] | [1 W, 2 W] |

We will assume that the algorithm which determines the $p_{\lambda,i}$ is linear of the type:

$$p_{\lambda1,1}(s_1)=0.5+0.2(1-0.5)=0.6 \text{ W}$$

$$p_{\lambda1,2}(s_2)=0.1+0.8(2-0.1)=1.62 \text{ W}$$

We will assume that the statistic function $P_S$ is an arithmetic mean. Therefore, we then have:

$$p_{\lambda1} = \frac{p_{\lambda1,1}+p_{\lambda1,2}}{2} = \frac{0.6+1.62}{2} = 1.11 \text{ W}$$

Similarly, we have:

$$p_{\lambda2,1}(s_1) = 0.1 + 0.2(0.2 - 0.1) = 0.12 W$$

$$p_{\lambda2,2}(s_1) = 1 + 0.8(2 - 1) = 1.8 W$$

$$p_{\lambda2} = \frac{p_{\lambda2,1}+p_{\lambda2,2}}{2} = \frac{0.12+1.8}{2} = 0.96 W$$

The power output in instant t=0, is:

$$P_s(\lambda_1,\lambda_2,s_1,s_2)=1.11+0.96=2.07 \text{ W}$$

We will assume that $T_{min}$=37.5° C., $T_{max}$=39.5° C.

The physician performs the pretreatment in an area of the body at $T_t$=38° C. The device indicates to change zone because $T_t$=38° C.>$T_{min}$.

The physician changes area and $T_t$=36.5° C. is read. The device starts the pretreatment, emitting a power P=1 W with $\lambda_1$, and the sensor measures an increment of:

$$\Delta T_{\lambda,1}=39.5-37.5=2° \text{ C}.$$

In a time of: $\Delta t_1$=10 s, thus obtaining a coefficient:

$$\alpha_{\lambda_1} = \frac{\Delta T_{\lambda_1}}{\Delta t}\frac{1}{p} = \frac{2}{10*1} = 0.2 \frac{°C.}{J}$$

Similarly, we will assume an increase of 2° C. is measured in 20 s for $\lambda_2$:

$$\alpha_{\lambda_2} = \frac{\Delta T_{\lambda_2}}{\Delta t}\frac{1}{p} = \frac{2}{201} = 0.1 \frac{°C.}{J}$$

It can be inferred that the patient's skin overheats with $\lambda_1$ faster than $\lambda_2$.

Example of Feedback Function G

We will assume that the function G is a feedback of the integral type. In this case, we have $$G(t, \alpha_{\lambda,i}, \Delta T, S_\rho) = K_1 \int_0^t \Delta T \frac{1}{\alpha_1} d\tau + K_2 \int_0^t \Delta T \frac{1}{\alpha_2} d\tau$$

We will assume that the function acts on the wavelengths where the effect desired by the physician is the lower of the two. Coefficients K1, K2 will be of the type:

$$K_1 = \frac{k_1}{s_1}, K_2 = \frac{k_2}{s_2}$$

with $k_1$, $k_2$ multiplication constants which stabilize the feedback system.

For example, assuming that the temperature sampling time is 3 seconds, if the temperature sensor measures an increase of 0.9° C. in the first sample and that the system is stable with $k_1$=0.05, $k_2$=0.1, we have:

$$G(t, \alpha_{\lambda,i}, \Delta T) =$$
$$\frac{k_1}{0,2}3\cdot 0,9 + \frac{k_2}{0,8}3\cdot 0,9 = 0,05\cdot 13,5 + 0,1\cdot 3,375 = \cong 0,68W + 0,38W$$

The feedback function G will lower the power of $\lambda_1$ by 0.68 W and $\lambda_2$ by 0.38 W.

In output we have:

$P_{tot} = P_s(\lambda_i, S_\rho) - G(t, \alpha_{\lambda_i}, \Delta T, S_\rho)$ $P_{tot} = (1.11 + 1.8) - (0.68 + 0.38)$ W $p_{\lambda 1} = 1.11 - 0.68 = 0.43$ W $p_{\lambda 2} = 0.96 - 0.38 = 0.58$ W

Frequency Calculation Example

We will assume that the "Biostimulation" effect $s_1$ is concentrated on high modulation frequencies (around 1 kHz), while the "Analgesic" effect $s_2$ is concentrated on low frequencies (around 10 Hz).

We will assume that the extension of the interval related to $\lambda_1$ is much greater than the one related to $\lambda_2$ because $\lambda_1$ is scarcely influential as the modulation frequency varies, and that the benefits of $\lambda_2$ are for a restricted interval of frequencies. We will have an empirical table of the type:

| tab(F) | $s_1$ | $s_2$ |
|---|---|---|
| $\lambda_1$ | Extended High $f$ | Extended Low $f$ |
| $\lambda_2$ | Restricted High $f$ | Restricted Low $f$ |

The following is desired:

$F_{1,1}\max = [1\text{ Hz}, 10\text{ kHz}]$ with $s_1=0$ $F_{1,1}\min = [1\text{ kHz}, 1\text{ kHz}]$ with $s_1=1$ $F_{1,2}\max = [1\text{ Hz}, 100\text{ Hz}]$ with $s_2=0$ $F_{1,2}\min = [5\text{ Hz}, 15\text{ Hz}]$ with $s_2=1$ $F_{2,1}\max = [900\text{ Hz}, 1.1\text{ kHz}]$ with $s_1=0$ $F_{2,1}\min = [1\text{ kHz}, 1\text{ kHz}]$ with $s_1=1$ $F_{2,2}\max = [9\text{ Hz}, 11\text{ Hz}]$ with $s_2=0$ $F_{2,2}\min = [10\text{ Hz}, 10\text{ Hz}]$ with $s_2=1$ The physician's choices were $S_1=0.2$, $S_2=0.8$.

Assuming that the interval varies in a linear manner, we have:

$F_{1,1} = [1 + 0.2*(1000-1), 10000 - 0.2*(10000-1000)]$ $F_{1,1} \cong [201\text{ Hz}, 8200\text{ Hz}]$ $F_{1,2} = [1 + 0.8*(5-1), 100 - 0.8*(100-15)]$ $F_{1,2} \cong [4\text{ Hz}, 32\text{ Hz}]$ $F_{2,1} = [900 + 0.2*(1000-900), 1100 - 0.2*(1100-1000)]$ $F_{2,1} \cong [920\text{ Hz}, 1080\text{ Hz}]$ $F_{2,2} = [10 + 0.8*(10-9), 11 - 0.8*(11-10)]$ $F_{2,2} \cong [10\text{ Hz}, 10\text{ Hz}]$ Table tab(F) becomes:

| tab(F) | $s_1 = 0.2$ | $s_2 = 0.8$ |
|---|---|---|
| $\lambda_1$ | [201, 8200]Hz | [4, 32]Hz |
| $\lambda_2$ | [920, 1080]Hz | [10, 10]Hz |

We will assume that the function FS acts on the sets intersection.

We have two disjoint intervals both for $\lambda_1$ and for $\lambda_2$.

We will assume that the average value is used for each interval:

$$f_{\lambda_1} = FS\left(\frac{8200+201}{2}, \frac{32+4}{2}\right) = 4200\text{ Hz}, 18\text{ Hz}$$

$$f_{\lambda_2} = FS\left(\frac{920+1080}{2}, \frac{10+10}{2}\right) = 1000\text{ Hz}, 10\text{ Hz}$$

A treatment $\Gamma$ will therefore be performed as a set of 2 steps:

$$\Gamma = \{\gamma_1, \gamma_2\}$$

$$\gamma_1 = \begin{bmatrix} \lambda_1 & p_{\lambda 1} & f_{\lambda 1}\delta_{\lambda 1} & e_{\lambda 1} \\ \lambda_2 & p_{\lambda 2} & f_{\lambda 2}\delta_{\lambda 2} & e_{\lambda 2} \end{bmatrix} = \begin{bmatrix} \lambda_1 & \ldots & 4200\text{ Hz} \ldots & e_{\lambda 1} \\ \lambda_2 & \ldots & 1000\text{ Hz} \ldots & e_{\lambda 2} \end{bmatrix}$$

$$\gamma_2 = \begin{bmatrix} \lambda_1 & p_{\lambda 1} & f_{\lambda 1}\delta_{\lambda 1} & e_{\lambda 1} \\ \lambda_2 & p_{\lambda 2} & f_{\lambda 2}\delta_{\lambda 2} & e_{\lambda 2} \end{bmatrix} = \begin{bmatrix} \lambda_1 & \ldots & 18\text{ Hz} \ldots & e_{\lambda 1} \\ \lambda_2 & \ldots & 10\text{ Hz} \ldots & e_{\lambda 2} \end{bmatrix}$$

If the choice had been:

| tab(F) | $s_1 = 0.2$ | $s_2 = 0.8$ |
|---|---|---|
| $\lambda_1$ | [1, 10k]Hz | [1, 100]Hz |
| $\lambda_2$ | [900, 1100]Hz | [9, 11]Hz | we would have two non-disjoint intervals for $\lambda_1$. We would have two disjoint intervals for $\lambda_2$. The total steps thus remain 2, where $\lambda_1$ will always emit the same frequency, while $\lambda_2$ will emit one frequency per step.

If FS acts on the central/average value of the intersection of the non-disjoint intervals, we have:

$$f_{\lambda_1} = FS\left(\frac{1+100}{2}\right) = FS(50) = 50\text{ Hz}$$

$$f_{\lambda_2} = FS\left(\frac{900+1100}{2}, \frac{9+11}{2}\right) = 1000\text{ Hz}, 10\text{ Hz}$$

and the steps become:

$$\gamma_1 = \begin{bmatrix} \lambda_1 & p_{\lambda 1} & f_{\lambda 1}\delta_{\lambda 1} & e_{\lambda 1} \\ \lambda_2 & p_{\lambda 2} & f_{\lambda 2}\delta_{\lambda 2} & e_{\lambda 2} \end{bmatrix} = \begin{bmatrix} \lambda_1 & \ldots & 50\text{ Hz} \ldots & e_{\lambda 1} \\ \lambda_2 & \ldots & 1000\text{ Hz} \ldots & e_{\lambda 2} \end{bmatrix}$$

$$\gamma_2 = \begin{bmatrix} \lambda_1 & p_{\lambda 1} & f_{\lambda 1}\delta_{\lambda 1} & e_{\lambda 1} \\ \lambda_2 & p_{\lambda 2} & f_{\lambda 2}\delta_{\lambda 2} & e_{\lambda 2} \end{bmatrix} = \begin{bmatrix} \lambda_1 & \ldots & 50\text{ Hz} \ldots & e_{\lambda 1} \\ \lambda_2 & \ldots & 10\text{ Hz} \ldots & e_{\lambda 2} \end{bmatrix}$$

Example of Energy Calculation

We will assume that little energy $\lambda_1$ is needed to have the "BIOSTIMULATION" effect and conversely that a lot of energy $\lambda_2$, is needed for the "ANALGESIC" effect:

| tab(E) | $s_1$ | $s_2$ |
|---|---|---|
| $\lambda_1$ | [20 J, 30 J] | [1 J, 3 J] |
| $\lambda_2$ | [1 J, 2 J] | [10, 15 J] |

We will assume that the algorithm which determines the $e_{\lambda,i}$ is linear of the type:

$$e_{\lambda 1,1}(s_1)=e_{\lambda 1,1}(0.2)=20+0.2(30-20)=22 \text{ J}$$

$$e_{\lambda 1,2}(s_2)=e_{\lambda 1,2}(0.8)=1+0.8(3-1)=2.6 \text{ J}$$

$$e_{\lambda 2,1}(s_1)=e_{\lambda 2,1}(0.2)=1+0.2(2-1)=1.2 \text{ J}$$

$$e_{\lambda 2,2}(s_2)=e_{\lambda 2,2}(0.8)=10+0.8(15-10)=14 \text{ J}$$

It is worth noting that the particular algorithm will be in general decided together with the physician who provides the treatment according to empirical results.

The total energy emitted by $\lambda_1$ must be:

$$e_{\lambda 1}=e_{\lambda 1,1}(s_1)+e_{\lambda 1,2}(s_2)=22+2.6=24.6 \text{ J}$$

$$e_{\lambda 2}=e_{\lambda 2,1}(s_1)+e_{\lambda 2,2}(s_2)=1.2+14=15.2 \text{ J}$$

The energies may be distributed in the various steps according to distribution algorithms (in general decided together with the physician who provides the treatment according to empirical results). For example, here we have chosen to subdivide the energies for each step in equal manner:

$$\gamma_1 = \begin{bmatrix} \lambda_1 & p_{\lambda 1} & f_{\lambda 1}\delta_{\lambda 1} & e_{\lambda 1} \\ \lambda_2 & p_{\lambda 2} & f_{\lambda 2}\delta_{\lambda 2} & e_{\lambda 2} \end{bmatrix} = \begin{bmatrix} \lambda_1 & 1.1W & 4200\,\text{Hz}\ldots & 12.3J \\ \lambda_2 & 0.96W & 1050\,\text{Hz}\ldots & 7.6J \end{bmatrix}$$

$$\gamma_2 = \begin{bmatrix} \lambda_1 & p_{\lambda 1} & f_{\lambda 1}\delta_{\lambda 1} & e_{\lambda 1} \\ \lambda_2 & p_{\lambda 2} & f_{\lambda 2}\delta_{\lambda 2} & e_{\lambda 2} \end{bmatrix} = \begin{bmatrix} \lambda_1 & 1.1W & 86\,\text{Hz}\ldots & 12.3J \\ \lambda_2 & 0.96W & 10\,\text{Hz}\ldots & 7.6J \end{bmatrix}$$

Another possible distribution algorithm may be that of associating with each step, each $$e_{\lambda i,j}(s_1) \in E_{i,j}, j=1\ldots r$$

In this case, we would have:

$$\gamma_1 = \begin{bmatrix} \lambda_1 & p_{\lambda 1} & f_{\lambda 1}\delta_{\lambda 1} & e_{\lambda 1} \\ \lambda_2 & p_{\lambda 2} & f_{\lambda 2}\delta_{\lambda 2} & e_{\lambda 2} \end{bmatrix} = \begin{bmatrix} \lambda_1 & 1.1W & 4200\,\text{Hz}\ldots & 22J \\ \lambda_2 & 0.96W & 1050\,\text{Hz}\ldots & 1.2J \end{bmatrix}$$

$$\gamma_2 = \begin{bmatrix} \lambda_1 & p_{\lambda 1} & f_{\lambda 1}\delta_{\lambda 1} & e_{\lambda 1} \\ \lambda_2 & p_{\lambda 2} & f_{\lambda 2}\delta_{\lambda 2} & e_{\lambda 2} \end{bmatrix} = \begin{bmatrix} \lambda_1 & 1.1W & 86\,\text{Hz}\ldots & 2.6J \\ \lambda_2 & 0.96W & 10\,\text{Hz}\ldots & 14J \end{bmatrix}$$

Device According to the Invention

Figure 9:
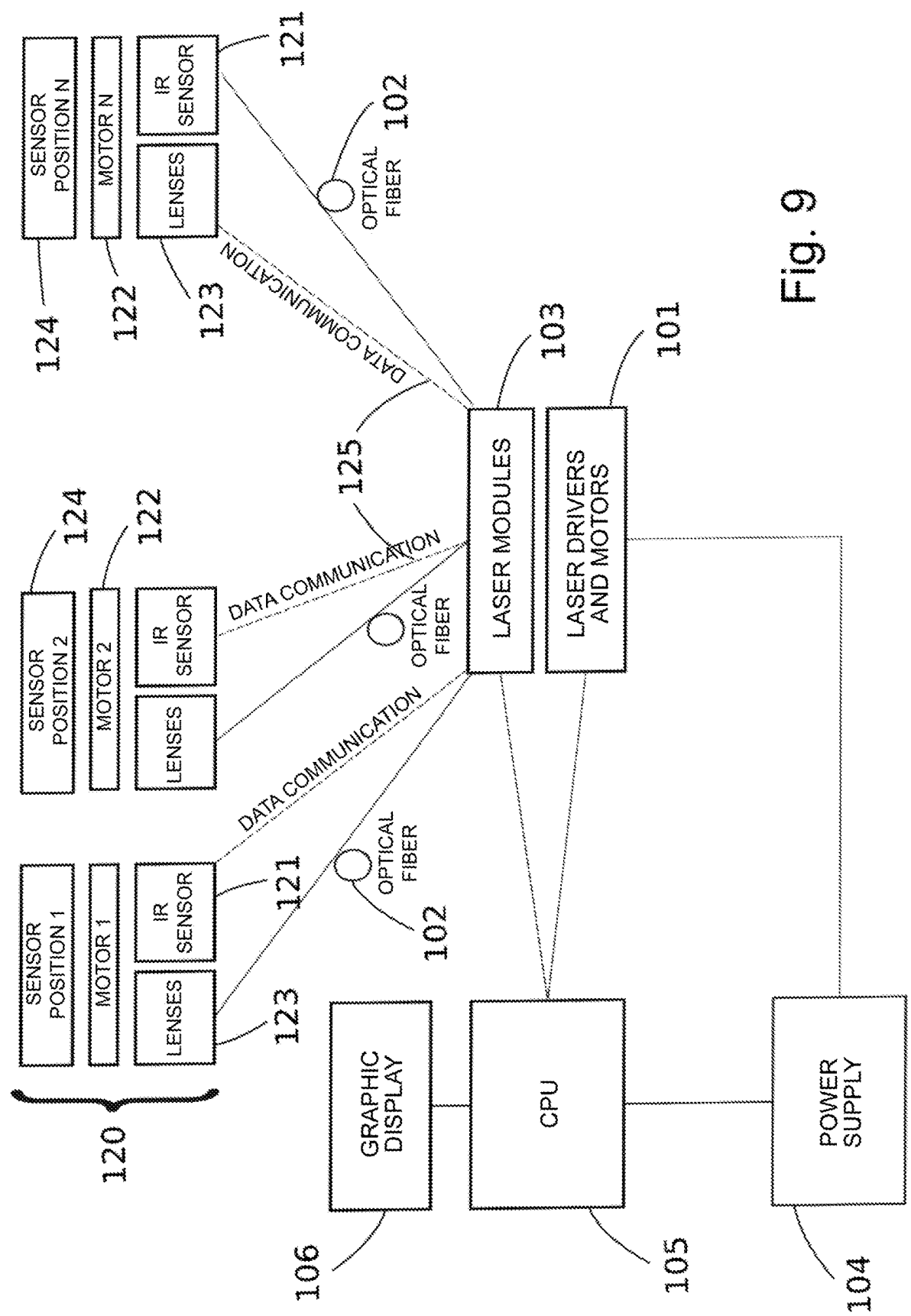
FIG. 9 shows a block chart of the apparatus according to the invention.

With reference to FIG. 9, in an embodiment of the invention, the multi-frequency laser device for skin treatment comprises a power supply unit 104, a CPU 105, a laser module 103 controlled by the CPU 105, a driver 101 which contributes to controlling the (one or more) laser modules 103.

To the CPU 105 may be connected a graphic screen 106.

The output of the laser modules 103 is sent by means of respective optical fibers 102 to respective heads 120 for skin application, provided with infrared sensor 121 (or other sensor) for measuring the temperature.

It is worth specifying here that the laser heads 120 do not contain the laser generation part, but only the end part of the optical fibers which depart from the laser module or modules 103 and possibly other sensors and/or devices which do not relate to laser beam generation. As a result, the laser heads are very light and in practice the method according to the present description moves the end parts of the optical fibers, with great energy savings and reduction of the risk of mechanical interference between the complete laser devices which are usually used in the prior art.

It is worth noting that the head is a motorized unit 122 controlled by computer (the CPU 105 itself, for example). The laser head receives the laser light from an electro-optical connector or optic fiber 102. The received light passes through one or more lenses 123 before reaching the skin.

A distance sensor 124 may be present in the laser head (distance between head and patient and/or position of the carriage along the arch).

The CPU 105 is connected to a data connection 125 to the head 120 to exchange data for the purposes of acquiring the instantaneous temperature and the distance/position.

Figure 10:
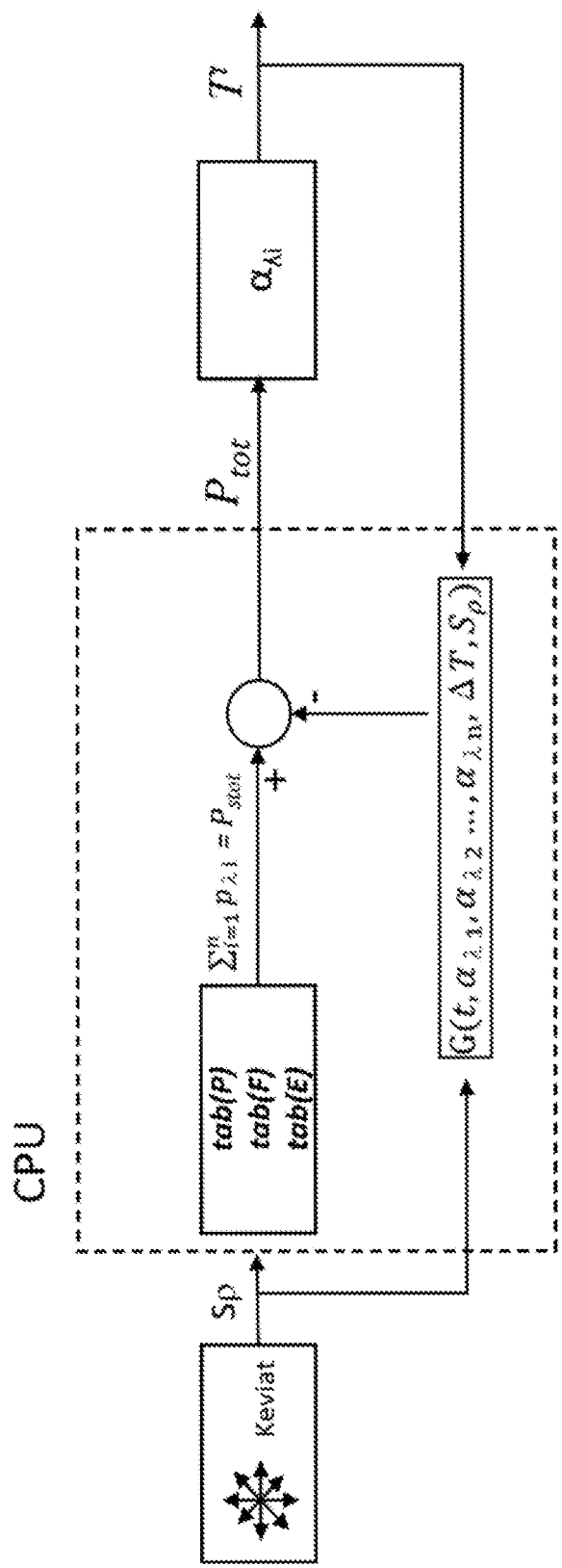
FIG. 10 shows a block and flow diagram which briefly describes the operation of the apparatus according to the invention.

FIG. 10 shows the feedback produced by the CPU 105. The Kiviat diagram data are acquired by the CPU which uses them to calculate the output power according to the method described above.

Using the pre-calculated skin absorption and the instantaneous skin temperature acquired by the sensor 121, the CPU calculates the correction function G and adjusts the power and other emission parameters in real time with a feedback cycle.

In this manner, both the patient's safety and the effectiveness of the therapy according to medical indications is ensured, by virtue of an entirely automatic adjustment (which therefore does not require the intervention of a physician during the therapy itself, which can be performed by other staff).

Scanning Apparatus According to the Invention

Figures from 11 to 14 illustrate an apparatus which implements the method referred to above, but which is also independent and may implement other methods. When implementing the method above, one or more laser heads with a temperature sensor are used.

Figure 11:
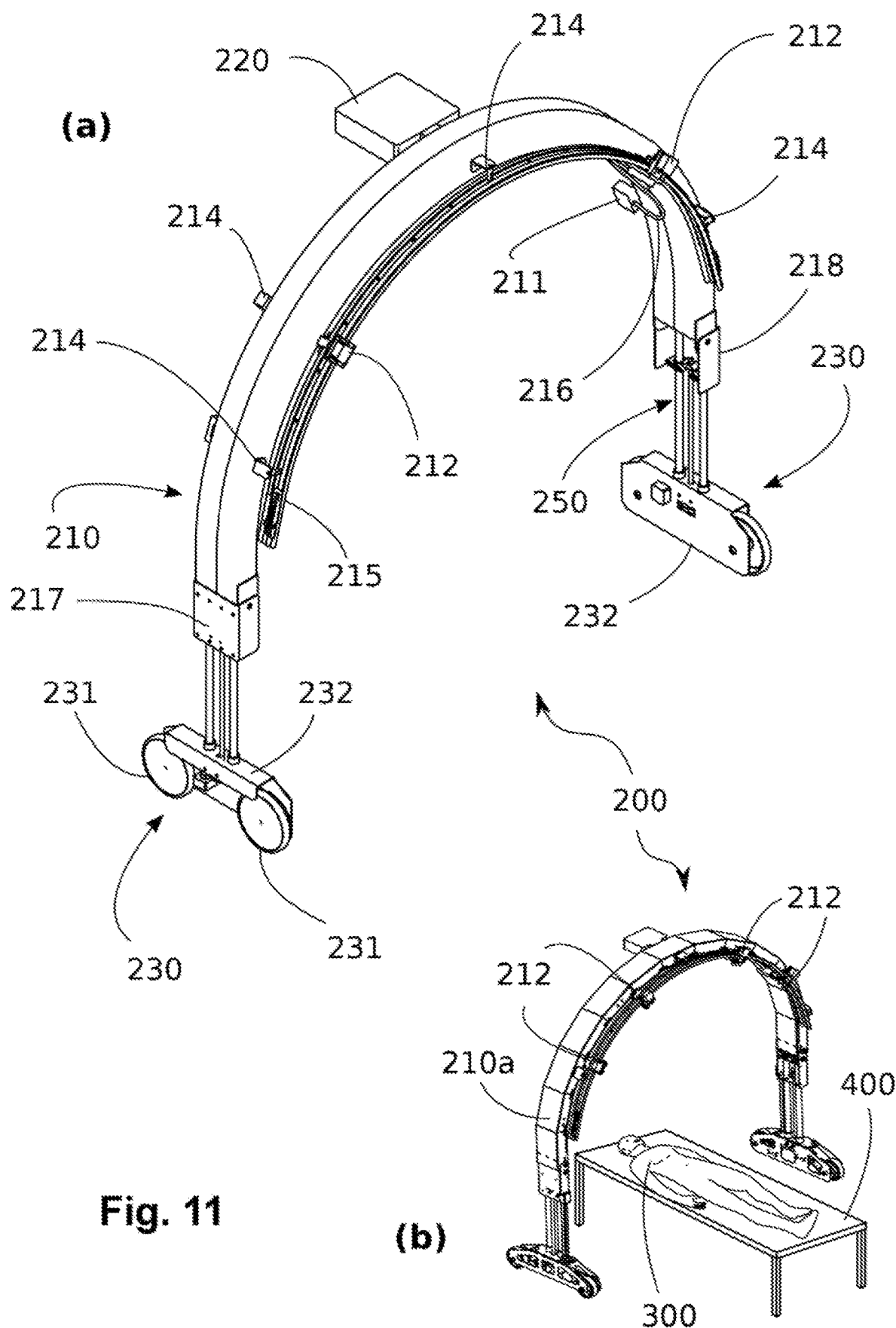
FIG. 11 shows a perspective view of the apparatus according to an embodiment of the present invention.
Figure 12:
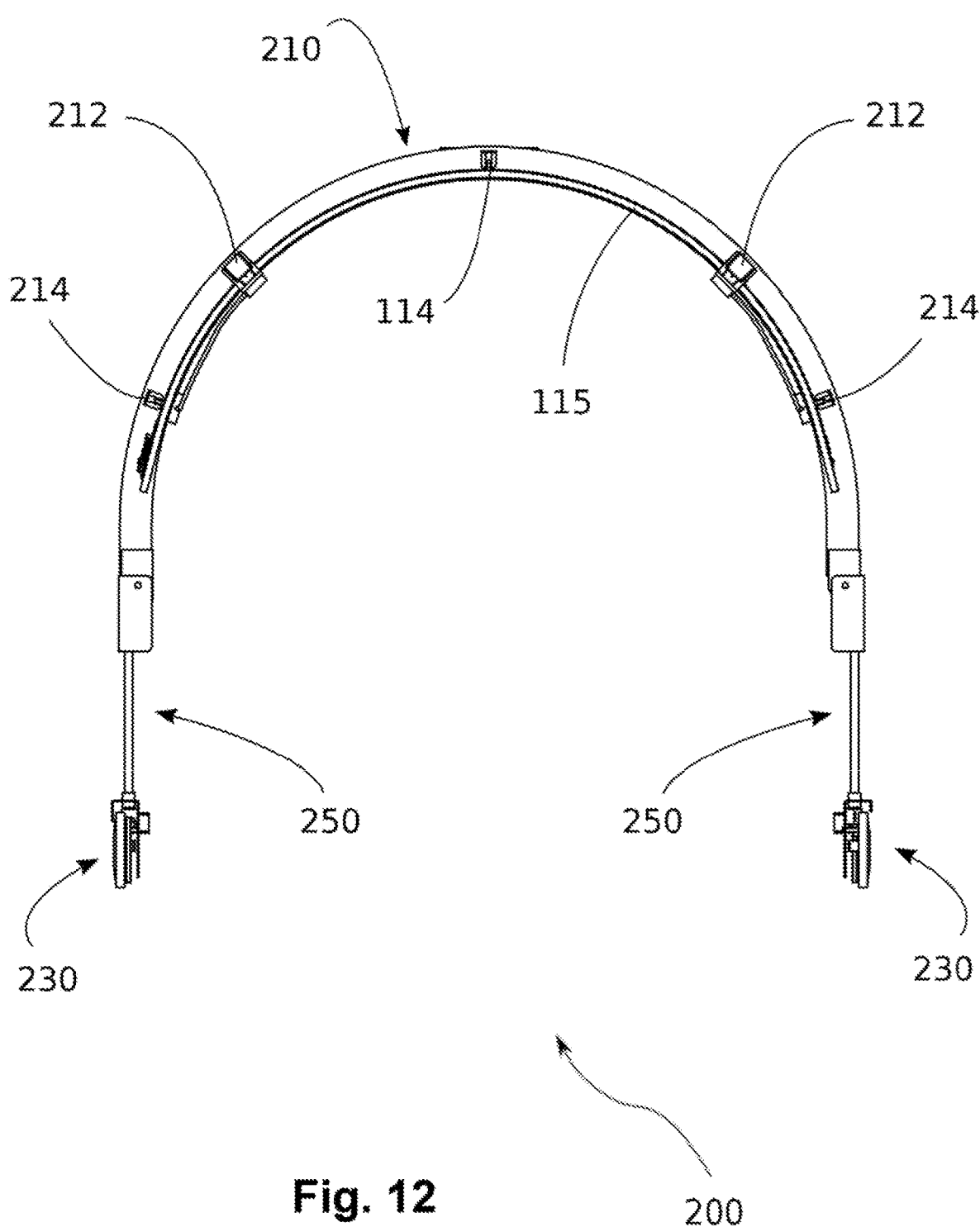
FIG. 12 shows a front view of the apparatus in FIG. 11.
Figure 13:
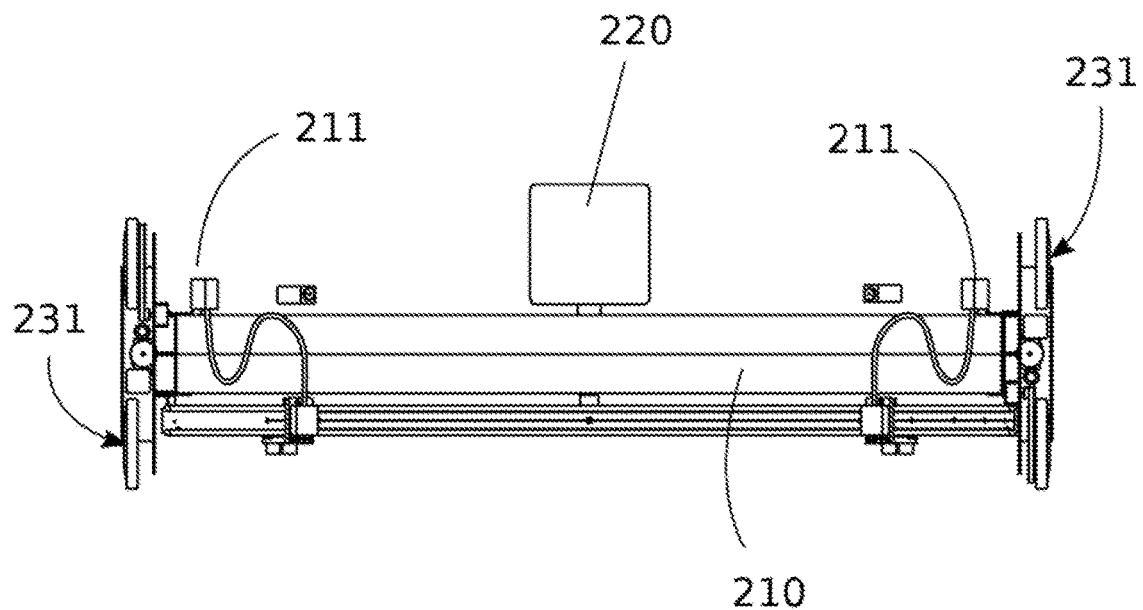
FIG. 13 shows a view from the bottom of the apparatus in FIG. 12.
Figure 14:
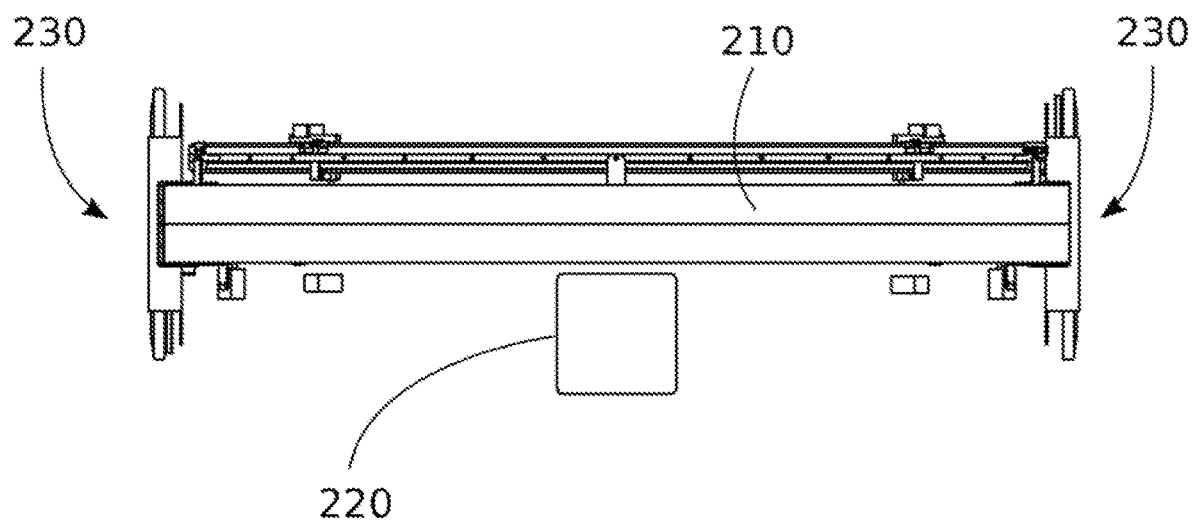
FIG. 14 shows a view from the top of the apparatus in FIG. 12.

The apparatus 200 for laser therapy of a patient 300, firstly comprises at least one arched support 210 which defines an arch, with a first arch end 217 and a second arch end 218. The arch may be continuous as in FIG. 11(a) or broken as in FIG. 11(b) according to constructive convenience.

The apparatus may also comprise a suspension system 230,250 of said at least one arched support 210. For example, the suspension system comprises moving means, e.g. a wheeled system or a sliding system on guides fixed to the patient's bed 400 (not shown) or other system. Optionally, there may be a vertical adjustment system 230 of the arched support. The vertical adjustment system may also comprise an ultrasound sensor (not shown) to calculate the distance of the arch from the specific patient.

Obviously, it comprises at least one laser generation unit 220 either connected or fixed to said at least one arched support 210.

One or more guides 215 are fixed along the arch of said at least one arched support 210.

At the end of the aforesaid laser emission, at least one laser head 212 is connected, by means of sliding connection means, on at least one of said one or more guides 215, said at least one laser head 212 having a respective laser emission direction towards the inside of said at least one arched support 210 (see below for further details).

Motorized means are present for moving said at least one laser head slidingly along at least one portion of said at least one of said one or more guides 215. The sliding extension will depend on the type of treatment, in all cases a sliding as wide as possible is preferable in order to be able to reach all the uncovered parts of the body, while the patient is on the bed 400.

At least one volumetric scanning sensor 214 is integrally connected to said at least one arched support 210 and is configured to detect a volume occupied by said patient, in use. This is important because the system needs to know where to direct the laser beams and in some cases patient's mass must be calculated. The volumetric scanning system is not a proximity sensor, which works in linear manner along a line, but a system which renders an entire volume, i.e. the three-dimensional shape of the patient on the bed. It may be a suitable camera or other sensor. In an embodiment, the volumetric scanning system comprises a series of TOF (Time Of Light) sensors distributed along the arch of the device. Given a correct distribution of the TOF (Time Of Light) sensors along the arch (practically, they are placed under the arch, e.g. by the side of where the laser fibers slide), the software of the device processes the data read by the sensors and reproduces a 3D scanner, both temporally and spatially. This is used to determine the best possible geometry and accuracy, obtaining the reconstruction of the spatial geometry of the patient's body. The proximity sensor may still be present because it performs an independent function, i.e. it is used during the treatment to ensure a uniform distance of the laser head from the patient. Instead, the volumetric sensor is usually used before the treatment for reconstructing the entire patient's shape and volume to see how deep the tissues to be treated are. Optionally, the volumetric sensor can be used to calculate the patient's volume and then the patient's average density, and then adjust the dose of laser energy to be administered on the basis of the average density of the body. The dose for the area can be calculated according to the body area to be treated.

According to the present description, it is possible and advantageous to calculate the minimum energy $e_{min}$ and the maximum energy $e_{max}$ on each axis of the Kiviat diagram described above and illustrated by correcting the value set by the physician with a coefficient which will be calculated on the basis of the detection of the volumetric sensor. Indeed, it is apparent that if the same energy were given to a hand and a belly, being the surface/volume ratio much higher in the hand, one runs the risk of side effects or a lower treatment effectiveness, respectively. Accordingly, the values for the hand must be lowered and the values for the belly must be raised according to their volume. A different correction is possible for each axis of the Kiviat diagram. The exact coefficients will be determined empirically, by measuring the volumes and the effects obtained on various subjects.

At least one temperature sensor for detecting, in use, an instantaneous temperature $T^r$ of the skin of said patient 300 under said arched support 210. Conveniently, an infrared sensor may be used.

Obviously, there is a central processing unit, which in the drawings is incorporated in the same housing 220 as the laser generator (but can also be placed in a different position), electronically connected to said at least one temperature sensor, to said at least one volumetric scanning sensor 214 and to said motorized means. A program is installed on the central unit 220 and configured to actuate said at least one laser generation unit 220 and said motorized means, on the basis of predefined data (e.g. therapy to be performed), the temperature detected by said at least one temperature sensor and of the data detected by said at least one volumetric scanning sensor 214.

There may also be a single guide. There may also be two laser heads 212 (regardless of the number of guides), each connected in sliding manner and moved by said motorized means on half of said single guide (or multiple guides), wherein said at least two laser heads 212 are optionally equipped with position sensors to avoid collisions between them.

There may be four (or more) laser heads, with the first two first laser heads 212 moved by said motorized means on (substantially) one half of said single guide, and two second laser heads 212 moved by said motorized means on the other (substantially) half of said single guide. Reference numeral 216 indicates the support for moving the connecting cables between the laser generator and the laser heads.

Figure 15:
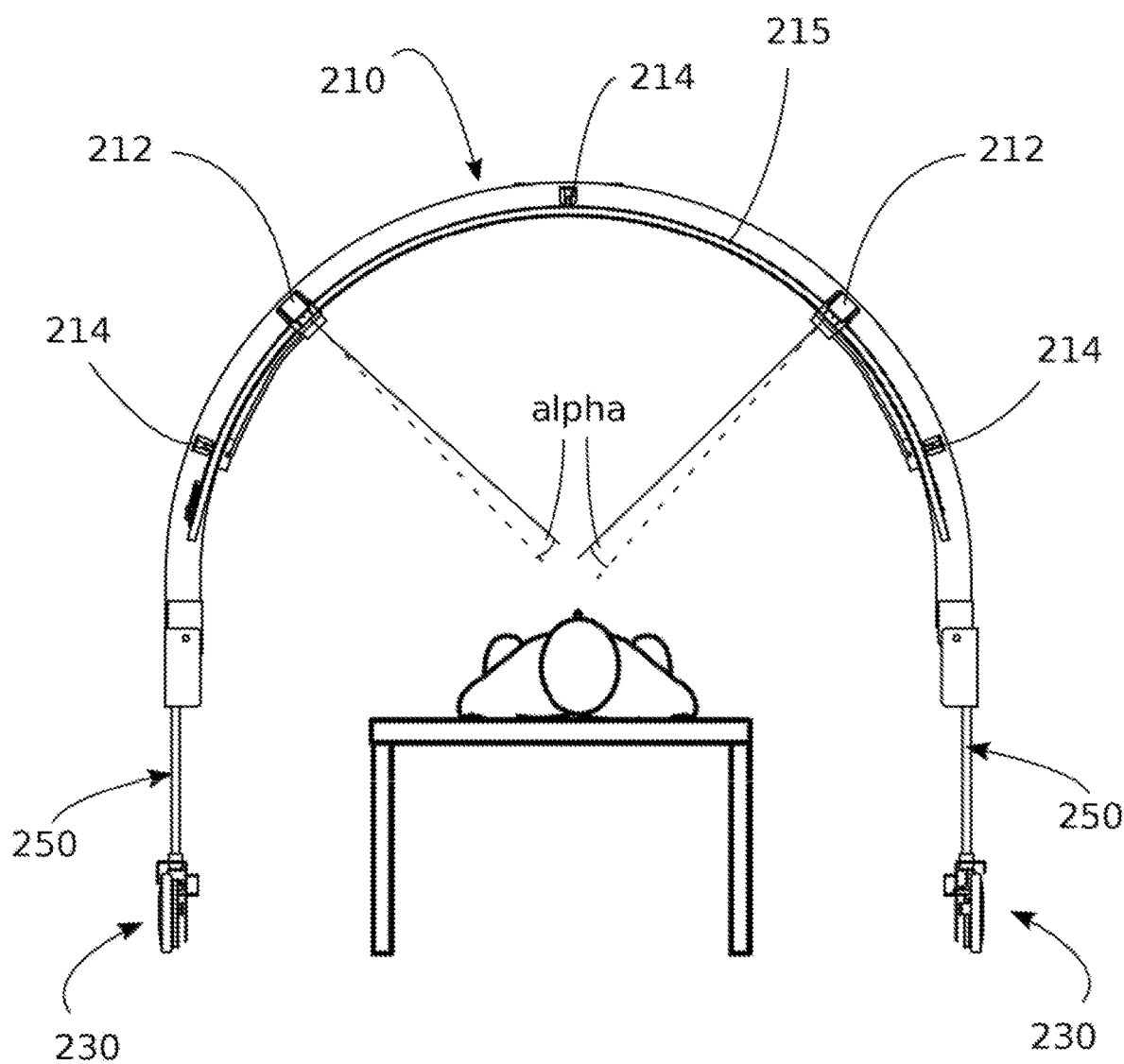
FIG. 15 shows a front view of a different embodiment of the apparatus according to the present invention.

Referring to FIG. 15, the laser emission directions of said at least two laser heads are inclined by an angle $\alpha$ with respect to the perpendicular to the tangent of said arch, wherein $\alpha$ is comprised between 0.1 and 7 sexagesimal degrees, in particular between 2 and 6 degrees, more particularly between 5 and 6 degrees. In this manner, when the laser heads are close together, they all contribute to the substantial irradiation of a single zone on the patient, whereby increasing the total irradiation power, and thus avoiding the need to use very powerful laser generators.

As mentioned above, the suspension system 230,250 consists of two sets of vertical guides 250 connected to two respective motorized wheel devices 230, the two sets of vertical guides being connected to said first end 217 and to said second end 218, respectively, so that said arched support 210 is adjustable in height with respect to said wheeled devices 230 by means of respective height adjustment systems (not shown), said motorized wheeled devices 230 and said respective height adjustment systems being operable by said central processing unit 220 according to said predefined data, the temperature detected by said at least one temperature sensor and of the data detected by said at least one volumetric scanning sensor 214.

The program installed on said central processing unit 220 is conveniently configured to actuate said at least one laser generating unit 220 and said motorized means on the basis of a dose to be supplied to the patient and calculated on the basis of the data detected by said at least one volumetric scanning sensor 214 and by said at least one temperature sensor and by predetermined information about the area of the patient to be treated.

Finally, a touchscreen interface can be advantageously provided on said arched support for setting a laser therapy plan.

Figure 16:
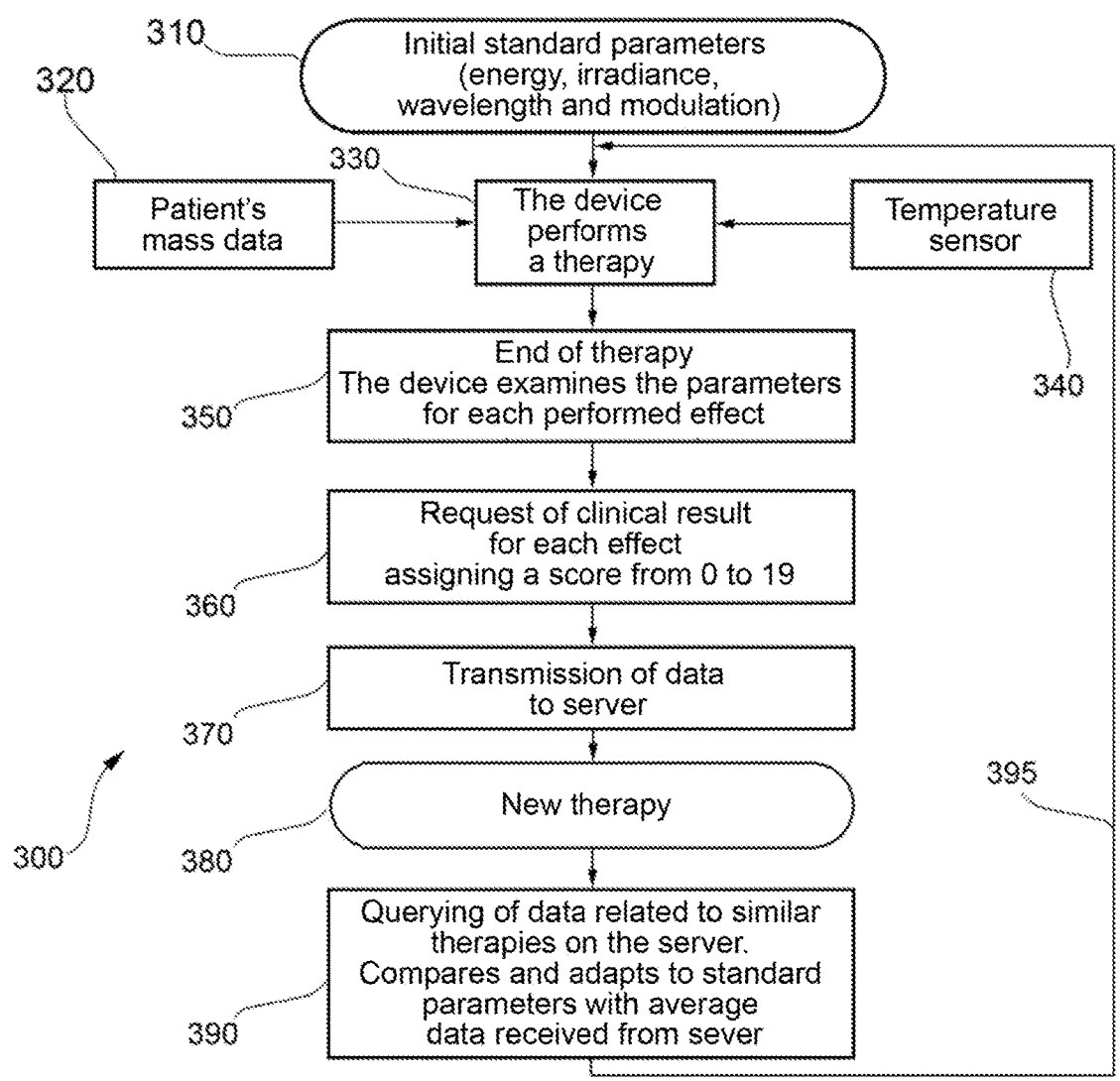
FIG. 16 shows a block chart of a method for updating and optimizing the therapeutic parameters.
Figure 17:
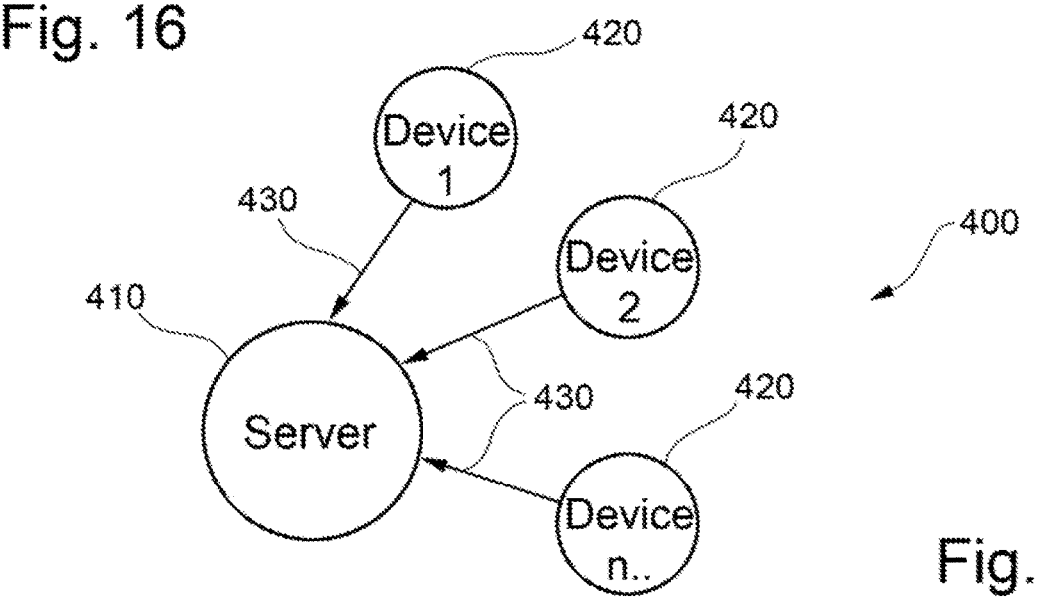
FIG. 17 shows a diagram of a system for updating and optimizing the therapeutic parameters using a plurality of machines connected to a server

Referring to FIGS. 16 and 17, according to an additional or alternative aspect of the present description, the system provides a system and a method for updating and optimizing the therapeutic parameters.

A plurality of machines 420 according to the present description form a system 400 and are connected either individually or in groups to a server 430 by means of connections 430, e.g. Internet connections.

An optimization algorithm 300 is responsible for updating the initial parameters 310 of each machine or group of machines. This takes place starting from the initial standard parameters 310, to which the data related to the patient's mass obtained by said volumetric sensor are added. With all these parameters, the machine performs a therapy in 330. At the end of the therapy, in 350, the device examines the parameters for each effect targeted by therapy. It asks the patient and/or the physician to provide a numerical assessment of the result of each targeted effect in 360 and these assessments are transmitted to the server in 370. A database is increased on the server in this manner by all the machines. In such a manner, at the time of a new therapy in 380, the method queries the database in 390 and the standard parameters are redefined on the basis of the data of all or part of the similar therapies. For example, standard parameters are reset in 395 as average parameters of the similar or identical therapies. The standard parameters may be, for example, energy, irradiance, wavelength and modulation.

Examples of questions asked for assessment are the following:

Analgesic effect: The device can ask for assessment immediately after the therapy and before the successive treatment.

Anti-inflammatory effect: The device can ask for assessment immediately after the therapy and before the successive treatment.

Antimicrobial effect: The device can ask for assessment immediately before the successive treatment only; this is because time is needed for the treatment to become effective.

Surface biosimulation effect: The device can ask for assessment immediately before the successive treatment only; this is because time is needed for the treatment to become effective.

The errors of any incorrect assessments provided to devices by therapists are automatically mitigated over time, because the comparison of the parameters of each single device occurs on the average of the parameters of all other devices; consequently, errors will be automatically canceled out over time, therapy after therapy.

This progressive group self-learning system on global level between the devices, independently and automatically, will transform a static therapy device into an intelligent device, which will increasingly optimize treatments more and more on its own, to approach a performance perfection which would not be achievable manually or with any other software system.

According to an additional or alternative aspect of the present description, the system in order to accomplish the aforesaid optimization or for other purposes, envisages the use of Artificial Intelligence routine, e.g. by means of Neural Networks or Convolutional Neural Networks, to optimize the treatment parameters autonomously, initially starting from a setting of standard or preset parameters.

For example, the Artificial Intelligence can optimize the questions for the aforesaid assessments according to the assessments of therapies themselves and/or according to other useful information.

These data allow the Artificial Intelligence to learn from past experiences of the same machine if similar conditions of the patient occur again.

The aforesaid database above is on a server, but it could be replicated locally. The artificial intelligence may also be local and/or on the server.

Importantly, the Artificial Intelligence must use the training data to recognize the best possible treatment (in terms of objective parameters of the therapeutic device, such as for example laser source parameters, irradiance, modulation, energy, wavelengths) for the individual patient on the basis of the intrinsic relations which it can obtain from the data.

The embodiment with the Artificial Intelligence provided on the single machine has the advantage of providing a complete machine, which needs to access data only.

In this manner, we have a progressive group self-learning system on global level between devices, independently and without a manual human contribution. The system, in this manner, is no longer operator-dependent and the physicians can optimize their clinical analysis and maximize the success of their care.

Example of the Laser Choice in the Apparatus

The first laser, L1, is at 660 nm and we have:
laser power: 100 mW (only for specifying the laser generator used)
Irradiance 50 mW/cm$^2$
Fluence 6 J/cm$^2$
Treatment time 120 s
The area of the spot is 2 cm$^2$, the diameter of the spot 16 mm.

The second laser, L2, is at 800 nm and we have:
laser power: 1 W (only for specifying the laser generator used)
Irradiance 200 mW/cm$^2$
Fluence 6 J/cm$^2$
Treatment time 30 s
The area of the spot is 5 cm$^2$, the diameter of the spot is about 25 mm.

The third laser, L3, is at 970 nm and we have:
laser power: 2.5 W (only for specifying the laser generator used)
Irradiance again 200 mW/cm$^2$
Fluence 6 J/cm$^2$
Treatment time 30 s.
The area of the spot is about 12.5 cm$^2$, the diameter of the spot is about 40 mm.

By optimizing the therapeutic parameters, it is possible to obtain multiple and different clinical benefits for the patient within the same treatment. All this guarantees maximum safety for the patient, whereby reducing possible risks of iatrogenic damage (possibly caused by the specialist due to an incorrect or inadequate pretreatment assessment which with this patent is no longer required). Moreover, by optimizing many benefits within the same treatment, the therapy times are considerably reduced both in biological terms for the patient and in economic terms for the professional. Obtaining any desired effect is visually represented by the machine in real time, peculiarity which guarantees the correct performance of the required treatment to the professional.

Hereto, we have described the preferred embodiments and suggested some variants of the present invention, but it is understood that a person skilled in the art can make modifications and changes without departing from the respective scope of protection, as defined by the appended claims.

The invention claimed is:

1. An apparatus for laser therapy of a patient, the apparatus comprising:
at least one arched support which defines an arch, with a first arch end and a second arch end;
a suspension system of said at least one arched support;
at least one laser generation unit connected to said at least one arched support, wherein said at least one laser generation unit is configured to generate a number n, n being a non-null positive integer, of laser beams with respective frequencies $\lambda_1, \lambda_2, \ldots \lambda_n$ to be sent to each of said at least one laser head;
one or more guides fixed along the arch of said at least one arched support;

at least one laser head separated from said at least one laser generation unit and connected to it by optical fibers the laser head being slidingly connected, on at least one of said one or more guides, said at least one laser head having a respective laser emission direction towards the inside of said at least one arched support;

motorized means for moving said at least one laser head slidingly along at least one portion of said at least one of said one or more guides;

at least one volumetric scanning sensor connected integrally to said at least one arched support, configured to detect a volume occupied by said patient, in use;

at least one temperature sensor for detecting, in use, an instantaneous temperature $T^t$ of said patient's skin under said arched support; and a central processing unit electronically connected to said at least one temperature sensor, to said at least one volumetric scanning sensor and to said motorized means, a program being installed on said central processing unit configured to actuate and/or adjust said at least one laser generation unit and said motorized means, on the basis of predetermined data, of temperature detected by said at least one temperature sensor and of data detected by said at least one volumetric scanning sensor, wherein said program comprises the following modules:

a first module A configured to acquire a set of user parameters $S=\{s_1, s_2, \ldots, s_r\}$ with $0 \leq s_j \leq 1$ and $j=1 \ldots r$, wherein r is a positive integer greater than 1;

a second module B configured to acquire an absorption coefficient $\alpha_{\lambda,i}$ of the patient's skin with respect to a wavelength $\lambda i$, for each $i=1 \ldots n$, wherein said module B comprises the following sub-modules:

a first sub-module configured to control said at least one laser generation unit to send said laser beams to a laser beam application unit, so that, during respective subsequent time intervals $Bt_i$ with $i=1 \ldots n$ the laser beams of respective wavelength $\lambda_1, \lambda_2, \ldots \lambda_n$ each with average power p are respectively and successively generated;

a second sub-module configured to detect, during each time interval $Bt_i$ of predetermined value, the temperature difference $\Delta T$ between a start temperature $T_{min}$ and an end temperature $T_{max}$ of the time interval $Bt_i$, as measured by said temperature sensor, or to set a predetermined temperature difference $\Delta T$ and take as the value of $Bt_i$ the time taken to pass from $T_{min}$ to $T_{max}$ as measured by said temperature sensor; and a third sub-module configured to calculate, on the basis of the values $Bt_i$ and $\Delta T$ as determined by the second sub-module, an absorption coefficient $\alpha_{\lambda,i}$ of the patient's skin with respect to the wavelength $\lambda_i$, for all $i=1 \ldots n$, wherein said absorption coefficient is calculated by said third sub-module according to the formula:

$$\alpha_{\lambda_i} = \frac{\Delta T_{\lambda_i}}{\Delta t} \frac{1}{p}$$
$$i = 1 \ldots n$$

wherein $\Delta t$ is the value of $Bt_i$ and $\Delta T_{\lambda,i}$ is the value of $\Delta T$ as determined for each wavelength $\lambda_i$, with $i=1 \ldots n$;

a third module C configured to control said laser generation unit to send said laser beams to said at least one laser head, after execution of said second module B, so as to generate the laser beams of respective wavelength $\lambda_1, \lambda_2, \ldots \lambda_n$ with respective powers $p_{\lambda,i}$ for $i=1, \ldots, n$ for various wavelengths and for a total power of all the laser beams given by the sum of:

a first fixed contribution corresponding to a value obtained on the basis of all the wavelengths $\lambda_1, \lambda_2, \ldots \lambda_n$ and of the parameters $S=\{s_1, s_2, \ldots, s_r\}$; and a second feedback instantaneous corrective contribution, obtained on the basis of time t elapsed since start of generation of the laser beams by module C, of all coefficients $\alpha_{\lambda,1}, \alpha_{\lambda,2}, \ldots, \alpha_{\lambda,n}$ of the temperature difference $\Delta T$ between a preset nominal temperature and the temperature $T^t$ detected by said at least one temperature sensor as well as of the parameters $S=\{s_1, s_2, \ldots, s_r\}$;

wherein said module C interrupts the generation of the laser beams when a preset time limit or a preset maximum radiated energy limit is reached.

2. The apparatus of claim 1, wherein there is a single guide and there are at least two laser heads each laser head being slidingly connected and moved by said motorized means on a half of said single guide only, wherein said at least two laser heads are optionally equipped with position sensors to prevent collisions one against the other.

3. The apparatus of claim 2, wherein there are four laser heads, with two first laser heads moved by said motorized means on one half of said single guide, and two second laser heads moved by said motorized means on the other half of said single guide.

4. The apparatus of claim 2, wherein respective laser emission directions of said at least two laser heads are inclined by an angle $\alpha$ with respect to the perpendicular to the tangent to said arch, wherein $\alpha$ is comprised between 0.1 and 7 sexagesimal degrees.

5. The apparatus of claim 1, wherein said suspension system is constituted by two sets of vertical guides connected to two respective wheeled motorized devices, the two sets of vertical guides being connected respectively to said first arch end and said second arch end so that said arched support is adjustable in height with respect to said wheeled devices by respective height adjustment systems, said wheeled motorized devices and said respective height adjustment systems being operable by said central processing unit on the basis of said predetermined data, of the temperature detected by said at least one temperature sensor and of data detected by said at least one volumetric scanning sensor.

6. The apparatus of claim 1, wherein said program installed on said central processing unit is configured to actuate said at least one laser generation unit and said motorized means on the basis of a dose to be supplied to the patient calculated on the basis of the data detected by said at least one volumetric scanning sensor and by said at least one temperature sensor and by predetermined information about an area of the patient to be treated.

7. The apparatus of claim 1, comprising, on said arched support, a touchscreen interface for setting a laser therapy plan.

8. The apparatus of claim 1, wherein said second sub-module, if said temperature sensor preliminarily detects a temperature $T^t$ lower than $T_{min}$, generates said laser beams until the temperature $T^t=T_{min}$ is reached and the time interval $Bt_i$ begins.

9. The apparatus of claim 1, wherein said absorption coefficient $\alpha_{\lambda,i}$, for each i=1 . . . n, has a preset value acquired from a memory or entered by a human-machine communication device.

10. The apparatus of claim 1, wherein the apparatus further comprises a physical internal memory or connection means to a remote physical memory, a look-up table tab(P) which provides a power value or interval $P_{i,j}$ for each parameter $s_j$ and each wavelength $\lambda_i$ being stored on said internal physical memory or in said remote physical memory, whereas if $P_{i,j}$ are power intervals $$P_{i,j}=[p_{min\ i,j}, p_{max\ i,j}]$$

is obtained, wherein $p_{min\ i,j}$ is the lower limit of said power interval which corresponds to $s_j=0$ and $p_{max\ i,j}$ is its upper value $s_j=1$, and wherein said power $p_{\lambda,i}$ is calculated on the basis of the power intervals of all the parameters $s_j$ for i= 1 . . . r.

11. The apparatus of claim 10, wherein said power value or interval $P_{i,j}$ is obtained in advance from empirical results or from initial estimates.

12. The apparatus of claim 10, wherein said power $p_{\lambda,i}$ is calculated by determining an effective value of each interval by using an interpolation function.

13. The apparatus of claim 1, wherein said laser beams have respectively an energy $e_{\lambda_i}$ for i=1 . . . , n, and wherein an internal physical memory or connection means to a remote physical memory are further comprised, a look-up table tab(E) which provides an energy value or interval $E_{i,j}$ for each parameter $s_j$ and for each wavelength $\lambda_i$ being stored on said internal physical memory or in said remote physical memory, whereas if $E_{i,j}$ are energy intervals $$E_{i,j}=[e_{min\ i,j}, e_{max\ i,j}]$$

is obtained, wherein $e_{min\ i,j}$ is the lower limit of said energy interval which corresponds to $s_j=0$ and $e_{max\ i,j}$ is its upper value for $s_j=1$, and wherein said energy $e_{\lambda,i}$ is calculated on the basis of the energy intervals of all the parameters $s_j$ for j=1 . . . r.

14. The apparatus of claim 13, wherein $e_{min\ i,j}$ and $e_{max\ i,j}$ are corrected on the basis of information detected by the volumetric sensor, on the basis of the surface-to-volume ratio of a specified body region to be subjected to laser therapy treatment.

15. The apparatus of claim 13, wherein said value or energy interval $E_{i,j}$ is obtained in advance by empirical results or from initial estimates.

16. The apparatus of claim 13, wherein said energy $e_{\lambda,i}$ is calculated by determining an effective value of each interval by using an interpolation function.

17. The apparatus of claim 1, wherein:
said laser beams have a modulation frequency $f_{\lambda_i}$, for i= 1, . . . , n respectively and wherein an internal physical memory or means for connection to a remote physical memory is further comprised, a look-up table tab(F) which provides a modulation frequency value or interval $F_{i,j}$ for each parameter $s_j$ and each wavelength $\lambda_i$ being stored on said internal physical memory or in said remote physical memory, whereas if $F_{i,j}$ are modulation frequency intervals $$F_{i,j}=[f_{min\ i,j}, f_{max\ i,j}]$$

is obtained, wherein $f_{min\ i,j}$ is the lower limit of said modulation frequency interval corresponding to $s_j=0$ and $f_{max\ i,j}$ is its upper value for $s_j=1$, and wherein said modulation frequency $f_{\lambda,i}$ is calculated on the basis of modulation frequency intervals of all the parameters $s_j$ for j=1 . . . r;
module C subdivides said laser beam generation into a number m of successive generations, wherein:
  m is the maximum number of disjoint subsets determined by the superposition of sets on each row of the table tab(F);
  for the respective m successive generations, respective modulation frequencies $f_{\lambda,i}$ calculated on the basis of a disjoint set or a non-null set as obtained in said superposition will result;
  the powers $p_{\lambda,i}$ are the same or different for the m successive generations; and
  said maximum energy or said time limit is subdivided over the m successive generations in either equal or different parts.

18. The apparatus of claim 17, wherein said value or modulation frequency interval $F_{i,j}$ is obtained in advance from empirical results or from initial estimates.

19. The apparatus of claim 17, wherein said modulation frequency $f_{\lambda,i}$ is calculated by determining an effective value of each interval by using an interpolation function.

20. The apparatus of claim 1, wherein, if the measured instantaneous temperature is higher than a threshold temperature, said at least one central processing unit adjusts power of said laser beams so as to remain below such threshold temperature, said central processing unit sending an alarm to an alarm peripheral device.

21. The apparatus of claim 1, wherein said parameters $S=\{s_1, s_2, \ldots, s_r\}$ are acquired by a graphic interface on which the coordinates of a Kiviat diagram are entered.

22. The apparatus of claim 1, wherein said at least one temperature sensor is an infrared radiation sensor.

23. The apparatus of claim 1, wherein each of said at least one volumetric scanning sensor is a camera associated with an ultrasonic sensor.

24. The apparatus of claim 1, wherein said temperature detected by said at least one temperature sensor is an average of temperatures detected by sensors of each laser head.

25. The apparatus of claim 1, wherein the apparatus further comprises:
  a module which includes an optimization or learning program;
  a connection to a central server on a telecommunications network;
  wherein the optimization or learning program is configured and adapted to:
  receive therapeutic treatment data sets from said central server performed by laser therapy apparatus of the same type as said apparatus for laser therapy;
  provide setup data of the apparatus for treatment on a specific patient, on the basis of said therapeutic treatment data sets and of parameters from sensors installed in said apparatus for laser therapy and related to said specific patient.

26. The apparatus of claim 25, wherein said optimization or learning program comprises artificial intelligence routines, able to:
  be trained to use said therapeutic treatment data sets; and
  provide the setup data of the apparatus for treatment on a specific patient, on the basis of setup parameters calculated using said therapeutic treatment data sets and of parameters from sensors installed in said apparatus for laser therapy and related to said specific patient.

27. The apparatus of claim 26, wherein training of the artificial intelligence is performed on the basis of information also obtained from a patient being treated.

28. The apparatus of claim 27, wherein the artificial intelligence is configured to generate and ask questions to the patient being treated on a dedicated interface to obtain information.

29. The apparatus of claim 1, wherein said second module B is configured to acquire said absorption coefficient $\alpha_{\lambda,I}$ by a preliminary assessment step or from a database.

* * * * *